(12) United States Patent
Meier

(10) Patent No.: US 7,846,680 B2
(45) Date of Patent: Dec. 7, 2010

(54) DETECTION OF THE NUCLEOLAR CHANNEL SYSTEM OF HUMAN ENDOMETRIUM AND USES THEREOF

(75) Inventor: U. Thomas Meier, New York, NY (US)

(73) Assignee: Albert Einstein College of Medicine of Yeshiva University, Bronx, NY (US)

( * ) Notice: Subject to any disclaimer, the term of this patent is extended or adjusted under 35 U.S.C. 154(b) by 46 days.

(21) Appl. No.: 12/321,603

(22) Filed: Jan. 22, 2009

(65) Prior Publication Data

US 2009/0215074 A1    Aug. 27, 2009

Related U.S. Application Data

(60) Provisional application No. 61/062,827, filed on Jan. 29, 2008.

(51) Int. Cl.
*G01N 33/53* (2006.01)
(52) U.S. Cl. .................... 435/7.1; 435/7.2; 436/518
(58) Field of Classification Search ................ None
See application file for complete search history.

(56) References Cited

U.S. PATENT DOCUMENTS 5,478,725 A    12/1995    Lessey

OTHER PUBLICATIONS

Dubowy R L et al., entitled "Improved endometrial assessment using cyclin E and p27," Fertility and Sterility, vol. 80, No. 1, Jul. 2003, 146-156.

Guffanti E et al., entitled "Nucleolar Channel Systems of Human Endometrial Epithelial Cells Mark the Preimplantation Window," abstract of poster presented at the 2nd SGI International Summit on Reproductive Medicine, Nov. 8-10, 2007 in Valencia, Spain.

Guffanti E et al., entitled "Nuclear pore complex proteins mark the implantation window in human endometrium," Journal of Cell Science, 121, 2008, 2037-2045.

Kittur N D, entitled "Studies on the Biogenesis of Two Nucleolar Entities: H/ACA RNPs and the Nucleolar Channel System," Ph.D. Thesis submitted to Albert Einstein College of Medicine of Yeshiva University, Jan. 2007, available to public May 2007, pp. i-170.

Kittur N, entitled "The Nucleolar Channel System of Human Endometrium Is Related to Endoplasmic Reticulum and R-Rings," Molecular Biology of the Cell, vol. 18, 2296-2304, Jun. 2007.

*Primary Examiner*—Jacob Cheu
(74) *Attorney, Agent, or Firm*—Amster, Rothstein & Ebenstein LLP

(57) ABSTRACT

Methods are disclosed for assaying at the light microscopic level for the presence or absence of nucleolar channel systems (NCSs) in an endometrial tissue sample, as are methods for determining whether or not a postovulatory human endometrium is in a state that is receptive for implantation of a human embryo, where the presence of NCSs indicates that the endometrium is in a state that is receptive for implantation of an embryo and the absence of NCSs indicates that the endometrium is not in a state that is receptive for implantation of the embryo, and methods for determining the effectiveness of a contraceptive in a woman, comprising assaying an endometrial tissue sample for the presence or absence of NCSs.

16 Claims, 5 Drawing Sheets

SEQUENCE LISTING

```
<160> NUMBER OF SEQ ID NOS: 13

<210> SEQ ID NO 1
<211> LENGTH: 1475
<212> TYPE: PRT
<213> ORGANISM: Homo sapiens

<400> SEQUENCE: 1

Met Ala Ser Gly Ala Gly Gly Val Gly Gly Gly Gly Gly Lys Ile
1               5                   10                  15

Arg Thr Arg Arg Cys His Gln Gly Pro Ile Lys Pro Tyr Gln Gln Gly
                20                  25                  30

Arg Gln Gln His Gln Gly Ile Leu Ser Arg Val Thr Glu Ser Val Lys
            35                  40                  45

Asn Ile Val Pro Gly Trp Leu Gln Arg Tyr Phe Asn Lys Asn Glu Asp
        50                  55                  60

Val Cys Ser Cys Ser Thr Asp Thr Ser Glu Val Pro Arg Trp Pro Glu
65                  70                  75                  80

Asn Lys Glu Asp His Leu Val Tyr Ala Asp Glu Glu Ser Ser Asn Ile
                85                  90                  95

Thr Asp Gly Arg Ile Thr Pro Glu Pro Ala Val Ser Asn Thr Glu Glu
                100                 105                 110

Pro Ser Thr Thr Ser Thr Ala Ser Asn Tyr Pro Asp Val Leu Thr Arg
            115                 120                 125

Pro Ser Leu His Arg Ser His Leu Asn Phe Ser Met Leu Glu Ser Pro
        130                 135                 140

Ala Leu His Cys Gln Pro Ser Thr Ser Ser Ala Phe Pro Ile Gly Ser
145                 150                 155                 160

Ser Gly Phe Ser Leu Val Lys Glu Ile Lys Asp Ser Thr Ser Gln His
                165                 170                 175

Asp Asp Asp Asn Ile Ser Thr Thr Ser Gly Phe Ser Ser Arg Ala Ser
                180                 185                 190

Asp Lys Asp Ile Thr Val Ser Lys Asn Thr Ser Leu Pro Pro Leu Trp
            195                 200                 205

Ser Pro Glu Ala Glu Arg Ser His Ser Leu Ser Gln His Thr Ala Thr
        210                 215                 220

Ser Ser Lys Lys Pro Ala Phe Asn Leu Ser Ala Phe Gly Thr Leu Ser
225                 230                 235                 240

Pro Ser Leu Gly Asn Ser Ser Ile Leu Lys Thr Ser Gln Leu Gly Asp
```

-continued

```
                245                 250                 255
Ser Pro Phe Tyr Pro Gly Lys Thr Thr Tyr Gly Gly Ala Ala Ala Ala
        260                 265                 270

Val Arg Gln Ser Lys Leu Arg Asn Thr Pro Tyr Gln Ala Pro Val Arg
        275                 280                 285

Arg Gln Met Lys Ala Lys Gln Leu Ser Ala Gln Ser Tyr Gly Val Thr
        290                 295                 300

Ser Ser Thr Ala Arg Arg Ile Leu Gln Ser Leu Glu Lys Met Ser Ser
305                 310                 315                 320

Pro Leu Ala Asp Ala Lys Arg Ile Pro Ser Ile Val Ser Ser Pro Leu
                325                 330                 335

Asn Ser Pro Leu Asp Arg Ser Gly Ile Asp Ile Thr Asp Phe Gln Ala
                340                 345                 350

Lys Arg Glu Lys Val Asp Ser Gln Tyr Pro Pro Val Gln Arg Leu Met
                355                 360                 365

Thr Pro Lys Pro Val Ser Ile Ala Thr Asn Arg Ser Val Tyr Phe Lys
    370                 375                 380

Pro Ser Leu Thr Pro Ser Gly Glu Phe Arg Lys Thr Asn Gln Arg Ile
385                 390                 395                 400

Asp Asn Lys Cys Ser Thr Gly Tyr Glu Lys Asn Met Thr Pro Gly Gln
                405                 410                 415

Asn Arg Glu Gln Arg Glu Ser Gly Phe Ser Tyr Pro Asn Phe Ser Leu
                420                 425                 430

Pro Ala Ala Asn Gly Leu Ser Ser Gly Val Gly Gly Gly Gly Gly Lys
                435                 440                 445

Met Arg Arg Glu Arg His Ala Phe Val Ala Ser Lys Pro Leu Glu Glu
    450                 455                 460

Glu Glu Met Glu Val Pro Val Leu Pro Lys Ile Ser Leu Pro Ile Thr
465                 470                 475                 480

Ser Ser Ser Leu Pro Thr Phe Asn Phe Ser Pro Glu Ile Thr Thr
                485                 490                 495

Ser Ser Pro Ser Pro Ile Asn Ser Ser Gln Ala Leu Thr Asn Lys Val
                500                 505                 510

Gln Met Thr Ser Pro Ser Ser Thr Gly Ser Pro Met Phe Lys Phe Ser
                515                 520                 525

Ser Pro Ile Val Lys Ser Thr Glu Ala Asn Val Leu Pro Pro Ser Ser
                530                 535                 540

Ile Gly Phe Thr Phe Ser Val Pro Val Ala Lys Thr Ala Glu Leu Ser
545                 550                 555                 560

Gly Ser Ser Ser Thr Leu Glu Pro Ile Ile Ser Ser Ser Ala His His
                565                 570                 575

Val Thr Thr Val Asn Ser Thr Asn Cys Lys Lys Thr Pro Pro Glu Asp
                580                 585                 590

Cys Glu Gly Pro Phe Arg Pro Ala Glu Ile Leu Lys Glu Gly Ser Val
                595                 600                 605

Leu Asp Ile Leu Lys Ser Pro Gly Phe Ala Ser Pro Lys Ile Asp Ser
                610                 615                 620

Val Ala Ala Gln Pro Thr Ala Thr Ser Pro Val Val Tyr Thr Arg Pro
625                 630                 635                 640

Ala Ile Ser Ser Phe Ser Ser Gly Ile Gly Phe Gly Glu Ser Leu
                645                 650                 655

Lys Ala Gly Ser Ser Trp Gln Cys Asp Thr Cys Leu Leu Gln Asn Lys
                660                 665                 670
```

-continued

```
Val Thr Asp Asn Lys Cys Ile Ala Cys Gln Ala Ala Lys Leu Ser Pro
        675                 680                 685

Arg Asp Thr Ala Lys Gln Thr Gly Ile Glu Thr Pro Asn Lys Ser Gly
        690                 695                 700

Lys Thr Thr Leu Ser Ala Ser Gly Thr Gly Phe Gly Asp Lys Phe Lys
705                 710                 715                 720

Pro Val Ile Gly Thr Trp Asp Cys Asp Thr Cys Leu Val Gln Asn Lys
                725                 730                 735

Pro Glu Ala Ile Lys Cys Val Ala Cys Glu Thr Pro Lys Pro Gly Thr
                740                 745                 750

Cys Val Lys Arg Ala Leu Thr Leu Thr Val Val Ser Glu Ser Ala Glu
        755                 760                 765

Thr Met Thr Ala Ser Ser Ser Cys Thr Val Thr Thr Gly Thr Leu
        770                 775                 780

Gly Phe Gly Asp Lys Phe Lys Arg Pro Ile Gly Ser Trp Glu Cys Ser
785                 790                 795                 800

Val Cys Cys Val Ser Asn Asn Ala Glu Asp Asn Lys Cys Val Ser Cys
                805                 810                 815

Met Ser Glu Lys Pro Gly Ser Ser Val Pro Ala Ser Ser Ser Ser Thr
                820                 825                 830

Val Pro Val Ser Leu Pro Ser Gly Gly Ser Leu Gly Leu Glu Lys Phe
                835                 840                 845

Lys Lys Pro Glu Gly Ser Trp Asp Cys Glu Leu Cys Leu Val Gln Asn
        850                 855                 860

Lys Ala Asp Ser Thr Lys Cys Leu Ala Cys Glu Ser Ala Lys Pro Gly
865                 870                 875                 880

Thr Lys Ser Gly Phe Lys Gly Phe Asp Thr Ser Ser Ser Ser Ser Asn
                885                 890                 895

Ser Ala Ala Ser Ser Ser Phe Lys Phe Gly Val Ser Ser Ser Ser Ser
        900                 905                 910

Gly Pro Ser Gln Thr Leu Thr Ser Thr Gly Asn Phe Lys Phe Gly Asp
        915                 920                 925

Gln Gly Gly Phe Lys Ile Gly Val Ser Ser Asp Ser Gly Ser Ile Asn
930                 935                 940

Pro Met Ser Glu Gly Phe Lys Phe Ser Lys Pro Ile Gly Asp Phe Lys
945                 950                 955                 960

Phe Gly Val Ser Ser Glu Ser Lys Pro Glu Glu Val Lys Lys Asp Ser
                965                 970                 975

Lys Asn Asp Asn Phe Lys Phe Gly Leu Ser Ser Gly Leu Ser Asn Pro
                980                 985                 990

Val Ser Leu Thr Pro Phe Gln Phe Gly Val Ser Asn Leu Gly Gln Glu
        995                 1000                1005

Glu Lys Lys Glu Glu Leu Pro Lys Ser Ser Ser Ala Gly Phe Ser
        1010                1015                1020

Phe Gly Thr Gly Val Ile Asn Ser Thr Pro Ala Pro Ala Asn Thr
        1025                1030                1035

Ile Val Thr Ser Glu Asn Lys Ser Ser Phe Asn Leu Gly Thr Ile
        1040                1045                1050

Glu Thr Lys Ser Ala Ser Val Ala Pro Phe Thr Cys Lys Thr Ser
        1055                1060                1065

Glu Ala Lys Lys Glu Glu Met Pro Ala Thr Lys Gly Gly Phe Ser
        1070                1075                1080
```

-continued

```
Phe Gly Asn Val Glu Pro Ala Ser Leu Pro Ser Ala Ser Val Phe
    1085                1090                1095

Val Leu Gly Arg Thr Glu Glu Lys Gln Gln Glu Pro Val Thr Ser
    1100                1105                1110

Thr Ser Leu Val Phe Gly Lys Lys Ala Asp Asn Glu Glu Pro Lys
    1115                1120                1125

Cys Gln Pro Val Phe Ser Gly Asn Ser Glu Gln Thr Lys Asp
    1130                1135                1140

Glu Asn Ser Ser Lys Ser Thr Phe Ser Phe Ser Met Thr Lys Pro
    1145                1150                1155

Ser Glu Lys Glu Ser Glu Gln Pro Ala Lys Ala Thr Phe Ala Phe
    1160                1165                1170

Gly Ala Gln Thr Ser Thr Thr Ala Asp Gln Gly Ala Ala Lys Pro
    1175                1180                1185

Val Phe Ser Phe Leu Asn Asn Ser Ser Ser Ser Ser Thr Pro
    1190                1195                1200

Ala Thr Ser Ala Gly Gly Gly Ile Phe Gly Ser Ser Thr Ser Ser
    1205                1210                1215

Ser Asn Pro Pro Val Ala Thr Phe Val Phe Gly Gln Ser Ser Asn
    1220                1225                1230

Pro Val Ser Ser Ser Ala Phe Gly Asn Thr Ala Glu Ser Ser Thr
    1235                1240                1245

Ser Gln Ser Leu Leu Phe Ser Gln Asp Ser Lys Leu Ala Thr Thr
    1250                1255                1260

Ser Ser Thr Gly Thr Ala Val Thr Pro Phe Val Phe Gly Pro Gly
    1265                1270                1275

Ala Ser Ser Asn Asn Thr Thr Thr Ser Gly Phe Gly Phe Gly Ala
    1280                1285                1290

Thr Thr Thr Ser Ser Ser Ala Gly Ser Ser Phe Val Phe Gly Thr
    1295                1300                1305

Gly Pro Ser Ala Pro Ser Ala Ser Pro Ala Phe Gly Ala Asn Gln
    1310                1315                1320

Thr Pro Thr Phe Gly Gln Ser Gln Gly Ala Ser Gln Pro Asn Pro
    1325                1330                1335

Pro Gly Phe Gly Ser Ile Ser Ser Ser Thr Ala Leu Phe Pro Thr
    1340                1345                1350

Gly Ser Gln Pro Ala Pro Pro Thr Phe Gly Thr Val Ser Ser Ser
    1355                1360                1365

Ser Gln Pro Pro Val Phe Gly Gln Gln Pro Ser Gln Ser Ala Phe
    1370                1375                1380

Gly Ser Gly Thr Thr Pro Asn Ser Ser Ser Ala Phe Gln Phe Gly
    1385                1390                1395

Ser Ser Thr Thr Asn Phe Asn Phe Thr Asn Asn Ser Pro Ser Gly
    1400                1405                1410

Val Phe Thr Phe Gly Ala Asn Ser Ser Thr Pro Ala Ala Ser Ala
    1415                1420                1425

Gln Pro Ser Gly Ser Gly Gly Phe Pro Phe Asn Gln Ser Pro Ala
    1430                1435                1440

Ala Phe Thr Val Gly Ser Asn Gly Lys Asn Val Phe Ser Ser Ser
    1445                1450                1455

Gly Thr Ser Phe Ser Gly Arg Lys Ile Lys Thr Ala Val Arg Arg
    1460                1465                1470

Arg Lys
```

1475

<210> SEQ ID NO 2
<211> LENGTH: 522
<212> TYPE: PRT
<213> ORGANISM: Homo sapiens

<400> SEQUENCE: 2

```
Met Ser Gly Phe Asn Phe Gly Gly Thr Gly Ala Pro Thr Gly Phe
1               5                   10                  15

Thr Phe Gly Thr Ala Lys Thr Ala Thr Thr Pro Ala Thr Gly Phe
            20                  25                  30

Ser Phe Ser Thr Ser Gly Thr Gly Gly Phe Asn Phe Gly Ala Pro Phe
            35                  40                  45

Gln Pro Ala Thr Ser Thr Pro Ser Thr Gly Leu Phe Ser Leu Ala Thr
50                  55                  60

Gln Thr Pro Ala Thr Gln Thr Thr Gly Phe Thr Phe Gly Thr Ala Thr
65                  70                  75                  80

Leu Ala Ser Gly Gly Thr Gly Phe Ser Leu Gly Ile Gly Ala Ser Lys
                85                  90                  95

Leu Asn Leu Ser Asn Thr Ala Ala Thr Pro Ala Met Ala Asn Pro Ser
                100                 105                 110

Gly Phe Gly Leu Gly Ser Ser Asn Leu Thr Asn Ala Ile Ser Ser Thr
            115                 120                 125

Val Thr Ser Ser Gln Gly Thr Ala Pro Thr Gly Phe Val Phe Gly Pro
            130                 135                 140

Ser Thr Thr Ser Val Ala Pro Ala Thr Thr Ser Gly Gly Phe Ser Phe
145                 150                 155                 160

Thr Gly Gly Ser Thr Ala Gln Pro Ser Gly Phe Asn Ile Gly Ser Ala
                165                 170                 175

Gly Asn Ser Ala Gln Pro Thr Ala Pro Ala Thr Leu Pro Phe Thr Pro
                180                 185                 190

Ala Thr Pro Ala Ala Thr Thr Ala Gly Ala Thr Gln Pro Ala Ala Pro
            195                 200                 205

Thr Pro Thr Ala Thr Ile Thr Ser Thr Gly Pro Ser Leu Phe Ala Ser
            210                 215                 220

Ile Ala Thr Ala Pro Thr Ser Ser Ala Thr Thr Gly Leu Ser Leu Cys
225                 230                 235                 240

Thr Pro Val Thr Thr Ala Gly Ala Pro Thr Ala Gly Thr Gln Gly Phe
                245                 250                 255

Ser Leu Lys Ala Pro Gly Ala Ala Ser Gly Thr Ser Thr Thr Thr Ser
                260                 265                 270

Thr Ala Ala Thr Ala Thr Ala Thr Thr Thr Ser Ser Ser Thr Thr
            275                 280                 285

Gly Phe Ala Leu Asn Leu Lys Pro Leu Ala Pro Ala Gly Ile Pro Ser
            290                 295                 300

Asn Thr Ala Ala Val Thr Ala Pro Pro Gly Pro Gly Ala Ala Ala
305                 310                 315                 320

Gly Ala Ala Ala Ser Ser Ala Met Thr Tyr Ala Gln Leu Glu Ser Leu
                325                 330                 335

Ile Asn Lys Trp Ser Leu Glu Leu Glu Asp Gln Glu Arg His Phe Leu
                340                 345                 350

Gln Gln Ala Thr Gln Val Asn Ala Trp Asp Arg Thr Leu Ile Glu Asn
            355                 360                 365
```

```
Gly Glu Lys Ile Thr Ser Leu His Arg Glu Val Glu Lys Val Lys Leu
    370                 375                 380
Asp Gln Lys Arg Leu Asp Gln Glu Leu Asp Phe Ile Leu Ser Gln Gln
385                 390                 395                 400
Lys Glu Leu Glu Asp Leu Leu Ser Pro Leu Glu Glu Leu Val Lys Glu
                405                 410                 415
Gln Ser Gly Thr Ile Tyr Leu Gln His Ala Asp Glu Glu Arg Glu Lys
            420                 425                 430
Thr Tyr Lys Leu Ala Glu Asn Ile Asp Ala Gln Leu Lys Arg Met Ala
        435                 440                 445
Gln Asp Leu Lys Asp Ile Ile Glu His Leu Asn Thr Ser Gly Ala Pro
    450                 455                 460
Ala Asp Thr Ser Asp Pro Leu Gln Gln Ile Cys Lys Ile Leu Asn Ala
465                 470                 475                 480
His Met Asp Ser Leu Gln Trp Ile Asp Gln Asn Ser Ala Leu Leu Gln
                485                 490                 495
Arg Lys Val Glu Glu Val Thr Lys Val Cys Glu Gly Arg Arg Lys Glu
            500                 505                 510
Gln Glu Arg Ser Phe Arg Ile Thr Phe Asp
    515                 520

<210> SEQ ID NO 3
<211> LENGTH: 2349
<212> TYPE: PRT
<213> ORGANISM: Homo sapiens

<400> SEQUENCE: 3

Met Ala Ala Val Leu Gln Gln Val Leu Glu Arg Thr Glu Leu Asn Lys
1               5                   10                  15
Leu Pro Lys Ser Val Gln Asn Lys Leu Glu Lys Phe Leu Ala Asp Gln
                20                  25                  30
Gln Ser Glu Ile Asp Gly Leu Lys Gly Arg His Glu Lys Phe Lys Val
            35                  40                  45
Glu Ser Glu Gln Gln Tyr Phe Glu Ile Glu Lys Arg Leu Ser His Ser
        50                  55                  60
Gln Glu Arg Leu Val Asn Glu Thr Arg Glu Cys Gln Ser Leu Arg Leu
65                  70                  75                  80
Glu Leu Glu Lys Leu Asn Asn Gln Leu Lys Ala Leu Thr Glu Lys Asn
                85                  90                  95
Lys Glu Leu Glu Ile Ala Gln Asp Arg Asn Ile Ala Ile Gln Ser Gln
            100                 105                 110
Phe Thr Arg Thr Lys Glu Glu Leu Glu Ala Glu Lys Arg Asp Leu Ile
        115                 120                 125
Arg Thr Asn Glu Arg Leu Ser Gln Glu Leu Glu Tyr Leu Thr Glu Asp
    130                 135                 140
Val Lys Arg Leu Asn Glu Lys Leu Lys Glu Ser Asn Thr Thr Lys Gly
145                 150                 155                 160
Glu Leu Gln Leu Lys Leu Asp Glu Leu Gln Ala Ser Asp Val Ser Val
                165                 170                 175
Lys Tyr Arg Glu Lys Arg Leu Glu Gln Glu Lys Glu Leu Leu His Ser
            180                 185                 190
Gln Asn Thr Trp Leu Asn Thr Glu Leu Lys Thr Lys Thr Asp Glu Leu
        195                 200                 205
Leu Ala Leu Gly Arg Glu Lys Gly Asn Glu Ile Leu Glu Leu Lys Cys
    210                 215                 220
```

```
Asn Leu Glu Asn Lys Lys Glu Val Ser Arg Leu Glu Glu Gln Met
225                 230                 235                 240

Asn Gly Leu Lys Thr Ser Asn Glu His Leu Gln Lys His Val Glu Asp
            245                 250                 255

Leu Leu Thr Lys Leu Lys Glu Ala Lys Glu Gln Gln Ala Ser Met Glu
            260                 265                 270

Glu Lys Phe His Asn Glu Leu Asn Ala His Ile Lys Leu Ser Asn Leu
        275                 280                 285

Tyr Lys Ser Ala Ala Asp Asp Ser Glu Ala Lys Ser Asn Glu Leu Thr
    290                 295                 300

Arg Ala Val Glu Glu Leu His Lys Leu Leu Lys Glu Ala Gly Glu Ala
305                 310                 315                 320

Asn Lys Ala Ile Gln Asp His Leu Leu Val Glu Gln Ser Lys Asp
            325                 330                 335

Gln Met Glu Lys Glu Met Leu Glu Lys Ile Gly Arg Leu Glu Lys Glu
            340                 345                 350

Leu Glu Asn Ala Asn Asp Leu Leu Ser Ala Thr Lys Arg Lys Gly Ala
        355                 360                 365

Ile Leu Ser Glu Glu Glu Leu Ala Ala Met Ser Pro Thr Ala Ala Ala
    370                 375                 380

Val Ala Lys Ile Val Lys Pro Gly Met Lys Leu Thr Glu Leu Tyr Asn
385                 390                 395                 400

Ala Tyr Val Glu Thr Gln Asp Gln Leu Leu Glu Lys Leu Glu Asn
            405                 410                 415

Lys Arg Ile Asn Lys Tyr Leu Asp Glu Ile Val Lys Glu Val Glu Ala
            420                 425                 430

Lys Ala Pro Ile Leu Lys Arg Gln Arg Glu Glu Tyr Glu Arg Ala Gln
        435                 440                 445

Lys Ala Val Ala Ser Leu Ser Val Lys Leu Glu Gln Ala Met Lys Glu
    450                 455                 460

Ile Gln Arg Leu Gln Glu Asp Thr Asp Lys Ala Asn Lys Gln Ser Ser
465                 470                 475                 480

Val Leu Glu Arg Asp Asn Arg Arg Met Glu Ile Gln Val Lys Asp Leu
            485                 490                 495

Ser Gln Gln Ile Arg Val Leu Leu Met Glu Leu Glu Glu Ala Arg Gly
        500                 505                 510

Asn His Val Ile Arg Asp Glu Glu Val Ser Ser Ala Asp Ile Ser Ser
    515                 520                 525

Ser Ser Glu Val Ile Ser Gln His Leu Val Ser Tyr Arg Asn Ile Glu
530                 535                 540

Glu Leu Gln Gln Gln Asn Gln Arg Leu Leu Val Ala Leu Arg Glu Leu
545                 550                 555                 560

Gly Glu Thr Arg Glu Arg Glu Glu Gln Glu Thr Thr Ser Ser Lys Ile
            565                 570                 575

Thr Glu Leu Gln Leu Lys Leu Glu Ser Ala Leu Thr Glu Leu Glu Gln
        580                 585                 590

Leu Arg Lys Ser Arg Gln His Gln Met Gln Leu Val Asp Ser Ile Val
    595                 600                 605

Arg Gln Arg Asp Met Tyr Arg Ile Leu Leu Ser Gln Thr Thr Gly Val
610                 615                 620

Ala Ile Pro Leu His Ala Ser Ser Leu Asp Asp Val Ser Leu Ala Ser
625                 630                 635                 640
```

```
Thr Pro Lys Arg Pro Ser Thr Ser Gln Thr Val Ser Thr Pro Ala Pro
            645             650             655

Val Pro Val Ile Glu Ser Thr Glu Ala Ile Glu Ala Lys Ala Ala Leu
            660             665             670

Lys Gln Leu Gln Glu Ile Phe Glu Asn Tyr Lys Glu Lys Ala Glu
            675             680             685

Asn Glu Lys Ile Gln Asn Glu Gln Leu Glu Lys Leu Gln Glu Gln Val
            690             695             700

Thr Asp Leu Arg Ser Gln Asn Thr Lys Ile Ser Thr Gln Leu Asp Phe
705             710             715             720

Ala Ser Lys Arg Tyr Glu Met Leu Gln Asp Asn Val Glu Gly Tyr Arg
            725             730             735

Arg Glu Ile Thr Ser Leu His Glu Arg Asn Gln Lys Leu Thr Ala Thr
            740             745             750

Thr Gln Lys Gln Glu Gln Ile Ile Asn Thr Met Thr Gln Asp Leu Arg
            755             760             765

Gly Ala Asn Glu Lys Leu Ala Val Ala Glu Val Arg Ala Glu Asn Leu
            770             775             780

Lys Lys Glu Lys Glu Met Leu Lys Leu Ser Val Arg Leu Ser Gln
785             790             795             800

Gln Arg Glu Ser Leu Leu Ala Glu Gln Arg Gly Gln Asn Leu Leu
            805             810             815

Thr Asn Leu Gln Thr Ile Gln Gly Ile Leu Glu Arg Ser Glu Thr Glu
            820             825             830

Thr Lys Gln Arg Leu Ser Ser Gln Ile Glu Lys Leu Glu His Glu Ile
            835             840             845

Ser His Leu Lys Lys Lys Leu Glu Asn Glu Val Glu Gln Arg His Thr
            850             855             860

Leu Thr Arg Asn Leu Asp Val Gln Leu Leu Asp Thr Lys Arg Gln Leu
865             870             875             880

Asp Thr Glu Thr Asn Leu His Leu Asn Thr Lys Glu Leu Leu Lys Asn
            885             890             895

Ala Gln Lys Glu Ile Ala Thr Leu Lys Gln His Leu Ser Asn Met Glu
            900             905             910

Val Gln Val Ala Ser Gln Ser Ser Gln Arg Thr Gly Lys Gly Gln Pro
            915             920             925

Ser Asn Lys Glu Asp Val Asp Asp Leu Val Ser Gln Leu Arg Gln Thr
            930             935             940

Glu Glu Gln Val Asn Asp Leu Lys Glu Arg Leu Lys Thr Ser Thr Ser
945             950             955             960

Asn Val Glu Gln Tyr Gln Ala Met Val Thr Ser Leu Glu Glu Ser Leu
            965             970             975

Asn Lys Glu Lys Gln Val Thr Glu Glu Val Arg Lys Asn Ile Glu Val
            980             985             990

Arg Leu Lys Glu Ser Ala Glu Phe Gln Thr Gln Leu Glu Lys Lys Leu
            995             1000            1005

Met Glu Val Glu Lys Glu Lys Gln Glu Leu Gln Asp Asp Lys Arg
            1010            1015            1020

Arg Ala Ile Glu Ser Met Glu Gln Gln Leu Ser Glu Leu Lys Lys
            1025            1030            1035

Thr Leu Ser Ser Val Gln Asn Glu Val Gln Glu Ala Leu Gln Arg
            1040            1045            1050

Ala Ser Thr Ala Leu Ser Asn Glu Gln Gln Ala Arg Arg Asp Cys
```

-continued

```
            1055                1060                1065
Gln Glu Gln Ala Lys Ile Ala Val Glu Ala Gln Asn Lys Tyr Glu
        1070                1075                1080

Arg Glu Leu Met Leu His Ala Ala Asp Val Glu Ala Leu Gln Ala
        1085                1090                1095

Ala Lys Glu Gln Val Ser Lys Met Ala Ser Val Arg Gln His Leu
        1100                1105                1110

Glu Glu Thr Thr Gln Lys Ala Glu Ser Gln Leu Leu Glu Cys Lys
        1115                1120                1125

Ala Ser Trp Glu Glu Arg Glu Arg Met Leu Lys Asp Glu Val Ser
        1130                1135                1140

Lys Cys Val Cys Arg Cys Glu Asp Leu Glu Lys Gln Asn Arg Leu
        1145                1150                1155

Leu His Asp Gln Ile Glu Lys Leu Ser Asp Lys Val Val Ala Ser
        1160                1165                1170

Val Lys Glu Gly Val Gln Gly Pro Leu Asn Val Ser Leu Ser Glu
        1175                1180                1185

Glu Gly Lys Ser Gln Glu Gln Ile Leu Glu Ile Leu Arg Phe Ile
        1190                1195                1200

Arg Arg Glu Lys Glu Ile Ala Glu Thr Arg Phe Glu Val Ala Gln
        1205                1210                1215

Val Glu Ser Leu Arg Tyr Arg Gln Arg Val Glu Leu Leu Glu Arg
        1220                1225                1230

Glu Leu Gln Glu Leu Glu Asp Ser Leu Asn Ala Glu Arg Glu Lys
        1235                1240                1245

Val Gln Val Thr Ala Lys Thr Met Ala Gln His Glu Glu Leu Met
        1250                1255                1260

Lys Lys Thr Glu Thr Met Asn Val Val Met Glu Thr Asn Lys Met
        1265                1270                1275

Leu Arg Glu Glu Lys Glu Arg Leu Glu Gln Asp Leu Gln Gln Met
        1280                1285                1290

Gln Ala Lys Val Arg Lys Leu Glu Leu Asp Ile Leu Pro Leu Gln
        1295                1300                1305

Glu Ala Asn Ala Glu Leu Ser Glu Lys Ser Gly Met Leu Gln Ala
        1310                1315                1320

Glu Lys Lys Leu Leu Glu Glu Asp Val Lys Arg Trp Lys Ala Arg
        1325                1330                1335

Asn Gln His Leu Val Ser Gln Lys Asp Pro Asp Thr Glu Glu
        1340                1345                1350

Tyr Arg Lys Leu Leu Ser Glu Lys Glu Val His Thr Lys Arg Ile
        1355                1360                1365

Gln Gln Leu Thr Glu Glu Ile Gly Arg Leu Lys Ala Glu Ile Ala
        1370                1375                1380

Arg Ser Asn Ala Ser Leu Thr Asn Asn Gln Asn Leu Ile Gln Ser
        1385                1390                1395

Leu Lys Glu Asp Leu Asn Lys Val Arg Thr Glu Lys Glu Thr Ile
        1400                1405                1410

Gln Lys Asp Leu Asp Ala Lys Ile Ile Asp Ile Gln Glu Lys Val
        1415                1420                1425

Lys Thr Ile Thr Gln Val Lys Lys Ile Gly Arg Arg Tyr Lys Thr
        1430                1435                1440

Gln Tyr Glu Glu Leu Lys Ala Gln Gln Asp Lys Val Met Glu Thr
        1445                1450                1455
```

```
Ser Ala Gln Ser Ser Gly Asp His Gln Glu Gln His Val Ser Val
    1460                1465                1470

Gln Glu Met Gln Glu Leu Lys Glu Thr Leu Asn Gln Ala Glu Thr
1475                1480                1485

Lys Ser Lys Ser Leu Glu Ser Gln Val Glu Asn Leu Gln Lys Thr
    1490                1495                1500

Leu Ser Glu Lys Glu Thr Glu Ala Arg Asn Leu Gln Glu Gln Thr
    1505                1510                1515

Val Gln Leu Gln Ser Glu Leu Ser Arg Leu Arg Gln Asp Leu Gln
    1520                1525                1530

Asp Arg Thr Thr Gln Glu Glu Gln Leu Arg Gln Gln Ile Thr Glu
    1535                1540                1545

Lys Glu Glu Lys Thr Arg Lys Ala Ile Val Ala Ala Lys Ser Lys
    1550                1555                1560

Ile Ala His Leu Ala Gly Val Lys Asp Gln Leu Thr Lys Glu Asn
    1565                1570                1575

Glu Glu Leu Lys Gln Arg Asn Gly Ala Leu Asp Gln Gln Lys Asp
    1580                1585                1590

Glu Leu Asp Val Arg Ile Thr Ala Leu Lys Ser Gln Tyr Glu Gly
    1595                1600                1605

Arg Ile Ser Arg Leu Glu Arg Glu Leu Arg Glu His Gln Glu Arg
    1610                1615                1620

His Leu Glu Gln Arg Asp Glu Pro Gln Glu Pro Ser Asn Lys Val
    1625                1630                1635

Pro Glu Gln Gln Arg Gln Ile Thr Leu Lys Thr Thr Pro Ala Ser
    1640                1645                1650

Gly Glu Arg Gly Ile Ala Ser Thr Ser Asp Pro Pro Thr Ala Asn
    1655                1660                1665

Ile Lys Pro Thr Pro Val Val Ser Thr Pro Ser Lys Val Thr Ala
    1670                1675                1680

Ala Ala Met Ala Gly Asn Lys Ser Thr Pro Arg Ala Ser Ile Arg
    1685                1690                1695

Pro Met Val Thr Pro Ala Thr Val Thr Asn Pro Thr Thr Thr Pro
    1700                1705                1710

Thr Ala Thr Val Met Pro Thr Thr Gln Val Glu Ser Gln Glu Ala
    1715                1720                1725

Met Gln Ser Glu Gly Pro Val Glu His Val Pro Val Phe Gly Ser
    1730                1735                1740

Thr Ser Gly Ser Val Arg Ser Thr Ser Pro Asn Val Gln Pro Ser
    1745                1750                1755

Ile Ser Gln Pro Ile Leu Thr Val Gln Gln Thr Gln Ala Thr
    1760                1765                1770

Ala Phe Val Gln Pro Thr Gln Gln Ser His Pro Gln Ile Glu Pro
    1775                1780                1785

Ala Asn Gln Glu Leu Ser Ser Asn Ile Val Glu Val Val Gln Ser
    1790                1795                1800

Ser Pro Val Glu Arg Pro Ser Thr Ser Thr Ala Val Phe Gly Thr
    1805                1810                1815

Val Ser Ala Thr Pro Ser Ser Ser Leu Pro Lys Arg Thr Arg Glu
    1820                1825                1830

Glu Glu Glu Asp Ser Thr Ile Glu Ala Ser Asp Gln Val Ser Asp
    1835                1840                1845
```

```
Asp Thr Val Glu Met Pro Leu Pro Lys Lys Leu Lys Ser Val Thr
    1850                1855                1860

Pro Val Gly Thr Glu Glu Val Met Ala Glu Glu Ser Thr Asp
    1865                1870                1875

Gly Glu Val Glu Thr Gln Val Tyr Asn Gln Asp Ser Gln Asp Ser
    1880                1885                1890

Ile Gly Glu Gly Val Thr Gln Gly Asp Tyr Thr Pro Met Glu Asp
    1895                1900                1905

Ser Glu Glu Thr Ser Gln Ser Leu Gln Ile Asp Leu Gly Pro Leu
    1910                1915                1920

Gln Ser Asp Gln Gln Thr Thr Thr Ser Ser Gln Asp Gly Gln Gly
    1925                1930                1935

Lys Gly Asp Asp Val Ile Val Ile Asp Ser Asp Glu Glu Glu
    1940                1945                1950

Asp Glu Glu Asp Asp Asp Asp Glu Asp Asp Thr Gly Met Gly
    1955                1960                1965

Asp Glu Gly Glu Asp Ser Asn Glu Gly Thr Gly Ser Ala Asp Gly
    1970                1975                1980

Asn Asp Gly Tyr Glu Ala Asp Asp Ala Glu Gly Gly Asp Gly Thr
    1985                1990                1995

Asp Pro Gly Thr Glu Thr Glu Glu Ser Met Gly Gly Gly Glu Gly
    2000                2005                2010

Asn His Arg Ala Ala Asp Ser Gln Asn Ser Gly Glu Gly Asn Thr
    2015                2020                2025

Gly Ala Ala Glu Ser Ser Phe Ser Gln Glu Val Ser Arg Glu Gln
    2030                2035                2040

Gln Pro Ser Ser Ala Ser Glu Arg Gln Ala Pro Arg Ala Pro Gln
    2045                2050                2055

Ser Pro Arg Arg Pro Pro His Pro Leu Pro Pro Arg Leu Thr Ile
    2060                2065                2070

His Ala Pro Pro Gln Glu Leu Gly Pro Pro Val Gln Arg Ile Gln
    2075                2080                2085

Met Thr Arg Arg Gln Ser Val Gly Arg Gly Leu Gln Leu Thr Pro
    2090                2095                2100

Gly Ile Gly Gly Met Gln Gln His Phe Phe Asp Asp Glu Asp Arg
    2105                2110                2115

Thr Val Pro Ser Thr Pro Thr Leu Val Val Pro His Arg Thr Asp
    2120                2125                2130

Gly Phe Ala Glu Ala Ile His Ser Pro Gln Val Ala Gly Val Pro
    2135                2140                2145

Arg Phe Arg Phe Gly Pro Pro Glu Asp Met Pro Gln Thr Ser Ser
    2150                2155                2160

Ser His Ser Asp Leu Gly Gln Leu Ala Ser Gln Gly Gly Leu Gly
    2165                2170                2175

Met Tyr Glu Thr Pro Leu Phe Leu Ala His Glu Glu Glu Ser Gly
    2180                2185                2190

Gly Arg Ser Val Pro Thr Thr Pro Leu Gln Val Ala Ala Pro Val
    2195                2200                2205

Thr Val Phe Thr Glu Ser Thr Thr Ser Asp Ala Ser Glu His Ala
    2210                2215                2220

Ser Gln Ser Val Pro Met Val Thr Thr Ser Thr Gly Thr Leu Ser
    2225                2230                2235

Thr Thr Asn Glu Thr Ala Thr Gly Asp Asp Gly Asp Glu Val Phe
```

```
                  2240                2245                2250

Val Glu Ala Glu Ser Glu Gly Ile Ser Ser Glu Ala Gly Leu Glu
        2255                2260                2265

Ile Asp Ser Gln Gln Glu Glu Pro Val Gln Ala Ser Asp Glu
    2270                2275                2280

Ser Asp Leu Pro Ser Thr Ser Gln Asp Pro Pro Ser Ser Ser
    2285                2290                2295

Val Asp Thr Ser Ser Ser Gln Pro Lys Pro Phe Arg Arg Val Arg
        2300                2305                2310

Leu Gln Thr Thr Leu Arg Gln Gly Val Arg Gly Arg Gln Phe Asn
        2315                2320                2325

Arg Gln Arg Gly Val Ser His Ala Met Gly Gly Arg Gly Gly Ile
        2330                2335                2340

Asn Arg Gly Asn Ile Asn
        2345

<210> SEQ ID NO 4
<211> LENGTH: 664
<212> TYPE: PRT
<213> ORGANISM: Homo sapiens

<400> SEQUENCE: 4

Met Glu Thr Pro Ser Gln Arg Arg Ala Thr Arg Ser Gly Ala Gln Ala
1               5                   10                  15

Ser Ser Thr Pro Leu Ser Pro Thr Arg Ile Thr Arg Leu Gln Glu Lys
            20                  25                  30

Glu Asp Leu Gln Glu Leu Asn Asp Arg Leu Ala Val Tyr Ile Asp Arg
        35                  40                  45

Val Arg Ser Leu Glu Thr Glu Asn Ala Gly Leu Arg Leu Arg Ile Thr
    50                  55                  60

Glu Ser Glu Glu Val Val Ser Arg Glu Val Ser Gly Ile Lys Ala Ala
65                  70                  75                  80

Tyr Glu Ala Glu Leu Gly Asp Ala Arg Lys Thr Leu Asp Ser Val Ala
                85                  90                  95

Lys Glu Arg Ala Arg Leu Gln Leu Glu Leu Ser Lys Val Arg Glu Glu
            100                 105                 110

Phe Lys Glu Leu Lys Ala Arg Asn Thr Lys Lys Glu Gly Asp Leu Ile
        115                 120                 125

Ala Ala Gln Ala Arg Leu Lys Asp Leu Glu Ala Leu Leu Asn Ser Lys
    130                 135                 140

Glu Ala Ala Leu Ser Thr Ala Leu Ser Glu Lys Arg Thr Leu Glu Gly
145                 150                 155                 160

Glu Leu His Asp Leu Arg Gly Gln Val Ala Lys Leu Glu Ala Ala Leu
                165                 170                 175

Gly Glu Ala Lys Lys Gln Leu Gln Asp Glu Met Leu Arg Arg Val Asp
            180                 185                 190

Ala Glu Asn Arg Leu Gln Thr Met Lys Glu Glu Leu Asp Phe Gln Lys
        195                 200                 205

Asn Ile Tyr Ser Glu Glu Leu Arg Glu Thr Lys Arg Arg His Glu Thr
    210                 215                 220

Arg Leu Val Glu Ile Asp Asn Gly Lys Gln Arg Glu Phe Glu Ser Arg
225                 230                 235                 240

Leu Ala Asp Ala Leu Gln Glu Leu Arg Ala Gln His Glu Asp Gln Val
                245                 250                 255
```

-continued

Glu Gln Tyr Lys Lys Glu Leu Glu Lys Thr Tyr Ser Ala Lys Leu Asp
                260                 265                 270

Asn Ala Arg Gln Ser Ala Glu Arg Asn Ser Asn Leu Val Gly Ala Ala
            275                 280                 285

His Glu Glu Leu Gln Gln Ser Arg Ile Arg Ile Asp Ser Leu Ser Ala
        290                 295                 300

Gln Leu Ser Gln Leu Gln Lys Gln Leu Ala Ala Lys Glu Ala Lys Leu
305                 310                 315                 320

Arg Asp Leu Glu Asp Ser Leu Ala Arg Glu Arg Asp Thr Ser Arg Arg
                325                 330                 335

Leu Leu Ala Glu Lys Glu Arg Glu Met Ala Glu Met Arg Ala Arg Met
            340                 345                 350

Gln Gln Gln Leu Asp Glu Tyr Gln Glu Leu Leu Asp Ile Lys Leu Ala
        355                 360                 365

Leu Asp Met Glu Ile His Ala Tyr Arg Lys Leu Leu Glu Gly Glu Glu
370                 375                 380

Glu Arg Leu Arg Leu Ser Pro Ser Pro Thr Ser Gln Arg Ser Arg Gly
385                 390                 395                 400

Arg Ala Ser Ser His Ser Ser Gln Thr Gln Gly Gly Gly Ser Val Thr
                405                 410                 415

Lys Lys Arg Lys Leu Glu Ser Thr Glu Ser Arg Ser Ser Phe Ser Gln
            420                 425                 430

His Ala Arg Thr Ser Gly Arg Val Ala Val Glu Glu Val Asp Glu Glu
        435                 440                 445

Gly Lys Phe Val Arg Leu Arg Asn Lys Ser Asn Glu Asp Gln Ser Met
    450                 455                 460

Gly Asn Trp Gln Ile Lys Arg Gln Asn Gly Asp Asp Pro Leu Leu Thr
465                 470                 475                 480

Tyr Arg Phe Pro Pro Lys Phe Thr Leu Lys Ala Gly Gln Val Val Thr
                485                 490                 495

Ile Trp Ala Ala Gly Ala Gly Ala Thr His Ser Pro Pro Thr Asp Leu
            500                 505                 510

Val Trp Lys Ala Gln Asn Thr Trp Gly Cys Gly Asn Ser Leu Arg Thr
        515                 520                 525

Ala Leu Ile Asn Ser Thr Gly Glu Glu Val Ala Met Arg Lys Leu Val
    530                 535                 540

Arg Ser Val Thr Val Val Glu Asp Asp Glu Asp Glu Asp Gly Asp Asp
545                 550                 555                 560

Leu Leu His His His His Gly Ser His Cys Ser Ser Ser Gly Asp Pro
                565                 570                 575

Ala Glu Tyr Asn Leu Arg Ser Arg Thr Val Leu Cys Gly Thr Cys Gly
            580                 585                 590

Gln Pro Ala Asp Lys Ala Ser Ala Ser Gly Ser Gly Ala Gln Val Gly
        595                 600                 605

Gly Pro Ile Ser Ser Gly Ser Ser Ala Ser Ser Val Thr Val Thr Arg
    610                 615                 620

Ser Tyr Arg Ser Val Gly Gly Ser Gly Gly Ser Phe Gly Asp Asn
625                 630                 635                 640

Leu Val Thr Arg Ser Tyr Leu Leu Gly Asn Ser Ser Pro Arg Thr Gln
                645                 650                 655

Ser Pro Gln Asn Cys Ser Ile Met
            660

<210> SEQ ID NO 5
<211> LENGTH: 600
<212> TYPE: PRT
<213> ORGANISM: Homo sapiens

<400> SEQUENCE: 5

```
Met Ala Thr Pro Leu Pro Gly Arg Ala Gly Gly Pro Ala Thr Pro Leu
1               5                   10                  15

Ser Pro Thr Arg Leu Ser Arg Leu Gln Glu Lys Glu Glu Leu Arg Glu
            20                  25                  30

Leu Asn Asp Arg Leu Ala His Tyr Ile Asp Arg Val Arg Ala Leu Glu
        35                  40                  45

Leu Glu Asn Asp Arg Leu Leu Leu Lys Ile Ser Lys Glu Glu Val
    50                  55                  60

Thr Thr Arg Glu Val Ser Gly Ile Lys Ala Leu Tyr Glu Ser Glu Leu
65                  70                  75                  80

Ala Asp Ala Arg Arg Val Leu Asp Glu Thr Ala Arg Glu Arg Ala Arg
                85                  90                  95

Leu Gln Ile Glu Ile Gly Lys Leu Arg Ala Glu Leu Asp Glu Val Asn
            100                 105                 110

Lys Ser Ala Lys Lys Arg Glu Gly Glu Leu Thr Val Ala Gln Gly Arg
        115                 120                 125

Val Lys Asp Leu Glu Ser Leu Phe His Arg Ser Glu Val Glu Leu Ala
    130                 135                 140

Ala Ala Leu Ser Asp Lys Arg Gly Leu Glu Ser Asp Val Ala Glu Leu
145                 150                 155                 160

Arg Ala Gln Leu Ala Lys Ala Glu Asp Gly His Ala Val Ala Lys Lys
                165                 170                 175

Gln Leu Glu Lys Glu Thr Leu Met Arg Val Asp Leu Glu Asn Arg Cys
            180                 185                 190

Gln Ser Leu Gln Glu Glu Leu Asp Phe Arg Lys Ser Val Phe Glu Glu
        195                 200                 205

Glu Val Arg Glu Thr Arg Arg His Glu Arg Arg Leu Val Glu Val
    210                 215                 220

Asp Ser Ser Arg Gln Gln Glu Tyr Asp Phe Lys Met Ala Gln Ala Leu
225                 230                 235                 240

Glu Glu Leu Arg Ser Gln His Asp Glu Gln Val Arg Leu Tyr Lys Leu
                245                 250                 255

Glu Leu Glu Gln Thr Tyr Gln Ala Lys Leu Asp Ser Ala Lys Leu Ser
            260                 265                 270

Ser Asp Gln Asn Asp Lys Ala Ala Ser Ala Ala Arg Glu Glu Leu Lys
        275                 280                 285

Glu Ala Arg Met Arg Leu Glu Ser Leu Ser Tyr Gln Leu Ser Gly Leu
    290                 295                 300

Gln Lys Gln Ala Ser Ala Ala Glu Asp Arg Ile Arg Glu Leu Glu Glu
305                 310                 315                 320

Ala Met Ala Gly Glu Arg Asp Lys Phe Arg Lys Met Leu Asp Ala Lys
                325                 330                 335

Glu Gln Glu Met Thr Glu Met Arg Asp Val Met Gln Gln Leu Ala
            340                 345                 350

Glu Tyr Gln Glu Leu Leu Asp Val Lys Leu Ala Leu Asp Met Glu Ile
        355                 360                 365

Asn Ala Tyr Arg Lys Leu Leu Glu Gly Glu Glu Glu Arg Leu Lys Leu
    370                 375                 380
```

```
Ser Pro Ser Pro Ser Ser Arg Val Thr Val Ser Arg Ala Thr Ser Ser
385                 390                 395                 400

Ser Ser Gly Ser Leu Ser Ala Thr Gly Arg Leu Gly Arg Ser Lys Arg
            405                 410                 415

Lys Arg Leu Glu Val Glu Glu Pro Leu Gly Ser Gly Pro Ser Val Leu
            420                 425                 430

Gly Thr Gly Thr Gly Gly Ser Gly Phe His Leu Ala Gln Gln Ala
        435                 440                 445

Ser Ala Ser Gly Ser Val Ser Ile Glu Glu Ile Asp Leu Glu Gly Lys
        450                 455                 460

Phe Val Gln Leu Lys Asn Asn Ser Asp Lys Asp Gln Ser Leu Gly Asn
465                 470                 475                 480

Trp Arg Ile Lys Arg Gln Val Leu Glu Gly Glu Ile Ala Tyr Lys
                485                 490                 495

Phe Thr Pro Lys Tyr Ile Leu Arg Ala Gly Gln Met Val Thr Val Trp
            500                 505                 510

Ala Ala Gly Ala Gly Val Ala His Ser Pro Pro Ser Thr Leu Val Trp
        515                 520                 525

Lys Gly Gln Ser Ser Trp Gly Thr Gly Glu Ser Phe Arg Thr Val Leu
530                 535                 540

Val Asn Ala Asp Gly Glu Glu Val Ala Met Arg Thr Val Lys Lys Ser
545                 550                 555                 560

Ser Val Met Arg Glu Asn Glu Asn Gly Glu Glu Glu Glu Glu Ala
                565                 570                 575

Glu Phe Gly Glu Glu Asp Leu Phe His Gln Gln Gly Asp Pro Arg Thr
            580                 585                 590

Thr Ser Arg Gly Cys Tyr Val Met
        595                 600

<210> SEQ ID NO 6
<211> LENGTH: 254
<212> TYPE: PRT
<213> ORGANISM: Homo sapiens

<400> SEQUENCE: 6

Met Asp Asn Tyr Ala Asp Leu Ser Asp Thr Glu Leu Thr Thr Leu Leu
1               5                   10                  15

Arg Arg Tyr Asn Ile Pro His Gly Pro Val Val Gly Ser Thr Arg Arg
            20                  25                  30

Leu Tyr Glu Lys Lys Ile Phe Glu Tyr Glu Thr Gln Arg Arg Arg Leu
        35                  40                  45

Ser Pro Pro Ser Ser Ser Ala Ala Ser Ser Tyr Ser Phe Ser Asp Leu
    50                  55                  60

Asn Ser Thr Arg Gly Asp Ala Asp Met Tyr Asp Leu Pro Lys Lys Glu
65              70                  75                  80

Asp Ala Leu Leu Tyr Gln Ser Lys Gly Tyr Asn Asp Asp Tyr Tyr Glu
                85                  90                  95

Glu Ser Tyr Phe Thr Thr Arg Thr Tyr Gly Glu Pro Glu Ser Ala Gly
            100                 105                 110

Pro Ser Arg Ala Val Arg Gln Ser Val Thr Ser Phe Pro Asp Ala Asp
        115                 120                 125

Ala Phe His His Gln Val His Asp Asp Leu Leu Ser Ser Glu
    130                 135                 140

Glu Glu Cys Lys Asp Arg Glu Arg Pro Met Tyr Gly Arg Asp Ser Ala
145                 150                 155                 160
```

```
Tyr Gln Ser Ile Thr His Tyr Arg Pro Val Ser Ala Ser Arg Ser Ser
                165                 170                 175

Leu Asp Leu Ser Tyr Tyr Pro Thr Ser Ser Ser Thr Ser Phe Met Ser
            180                 185                 190

Ser Ser Ser Ser Ser Ser Ser Trp Leu Thr Arg Arg Ala Ile Arg Pro
        195                 200                 205

Glu Asn Arg Ala Pro Gly Ala Gly Leu Gly Gln Asp Arg Gln Val Pro
    210                 215                 220

Leu Trp Gly Gln Leu Leu Leu Phe Leu Val Phe Val Ile Val Leu Phe
225                 230                 235                 240

Phe Ile Tyr His Phe Met Gln Ala Glu Glu Gly Asn Pro Phe
                245                 250

<210> SEQ ID NO 7
<211> LENGTH: 592
<212> TYPE: PRT
<213> ORGANISM: Homo sapiens

<400> SEQUENCE: 7

Met Glu Gly Lys Trp Leu Leu Cys Met Leu Leu Val Leu Gly Thr Ala
1               5                   10                  15

Ile Val Glu Ala His Asp Gly His Asp Asp Asp Val Ile Asp Ile Glu
            20                  25                  30

Asp Asp Leu Asp Asp Val Ile Glu Glu Val Glu Asp Ser Lys Pro Asp
        35                  40                  45

Thr Thr Ala Pro Pro Ser Ser Pro Lys Val Thr Tyr Lys Ala Pro Val
    50                  55                  60

Pro Thr Gly Glu Val Tyr Phe Ala Asp Ser Phe Asp Arg Gly Thr Leu
65                  70                  75                  80

Ser Gly Trp Ile Leu Ser Lys Ala Lys Lys Asp Asp Thr Asp Asp Glu
                85                  90                  95

Ile Ala Lys Tyr Asp Gly Lys Trp Glu Val Glu Glu Met Lys Glu Ser
            100                 105                 110

Lys Leu Pro Gly Asp Lys Gly Leu Val Leu Met Ser Arg Ala Lys His
        115                 120                 125

His Ala Ile Ser Ala Lys Leu Asn Lys Pro Phe Leu Phe Asp Thr Lys
    130                 135                 140

Pro Leu Ile Val Gln Tyr Glu Val Asn Phe Gln Asn Gly Ile Glu Cys
145                 150                 155                 160

Gly Gly Ala Tyr Val Lys Leu Leu Ser Lys Thr Pro Glu Leu Asn Leu
                165                 170                 175

Asp Gln Phe His Asp Lys Thr Pro Tyr Thr Ile Met Phe Gly Pro Asp
            180                 185                 190

Lys Cys Gly Glu Asp Tyr Lys Leu His Phe Ile Phe Arg His Lys Asn
        195                 200                 205

Pro Lys Thr Gly Ile Tyr Glu Glu Lys His Ala Lys Arg Pro Asp Ala
    210                 215                 220

Asp Leu Lys Thr Tyr Phe Thr Asp Lys Lys Thr His Leu Tyr Thr Leu
225                 230                 235                 240

Ile Leu Asn Pro Asp Asn Ser Phe Glu Ile Leu Val Asp Gln Ser Val
                245                 250                 255

Val Asn Ser Gly Asn Leu Leu Asn Asp Met Thr Pro Pro Val Asn Pro
            260                 265                 270

Ser Arg Glu Ile Glu Asp Pro Glu Asp Arg Lys Pro Glu Asp Trp Asp
```

-continued

```
                275                 280                 285
Glu Arg Pro Lys Ile Pro Asp Pro Glu Ala Val Lys Pro Asp Asp Trp
    290                 295                 300
Asp Glu Asp Ala Pro Ala Lys Ile Pro Asp Glu Glu Ala Thr Lys Pro
305                 310                 315                 320
Glu Gly Trp Leu Asp Asp Glu Pro Glu Tyr Val Pro Asp Pro Asp Ala
                325                 330                 335
Glu Lys Pro Glu Asp Trp Asp Glu Asp Met Asp Gly Glu Trp Glu Ala
            340                 345                 350
Pro Gln Ile Ala Asn Pro Arg Cys Glu Ser Ala Pro Gly Cys Gly Val
                355                 360                 365
Trp Gln Arg Pro Val Ile Asp Asn Pro Asn Tyr Lys Gly Lys Trp Lys
            370                 375                 380
Pro Pro Met Ile Asp Asn Pro Ser Tyr Gln Gly Ile Trp Lys Pro Arg
385                 390                 395                 400
Lys Ile Pro Asn Pro Asp Phe Phe Glu Asp Leu Glu Pro Phe Arg Met
                405                 410                 415
Thr Pro Phe Ser Ala Ile Gly Leu Glu Leu Trp Ser Met Thr Ser Asp
            420                 425                 430
Ile Phe Phe Asp Asn Phe Ile Ile Cys Ala Asp Arg Arg Ile Val Asp
                435                 440                 445
Asp Trp Ala Asn Asp Gly Trp Gly Leu Lys Lys Ala Ala Asp Gly Ala
            450                 455                 460
Ala Glu Pro Gly Val Val Gly Gln Met Ile Glu Ala Ala Glu Glu Arg
465                 470                 475                 480
Pro Trp Leu Trp Val Val Tyr Ile Leu Thr Val Ala Leu Pro Val Phe
                485                 490                 495
Leu Val Ile Leu Phe Cys Cys Ser Gly Lys Lys Gln Thr Ser Gly Met
            500                 505                 510
Glu Tyr Lys Lys Thr Asp Ala Pro Gln Pro Asp Val Lys Glu Glu Glu
                515                 520                 525
Glu Glu Lys Glu Glu Lys Asp Lys Gly Asp Glu Glu Glu Glu Glu Gly
            530                 535                 540
Glu Glu Lys Leu Glu Glu Lys Gln Lys Ser Asp Ala Glu Glu Asp Gly
545                 550                 555                 560
Gly Thr Val Ser Gln Glu Glu Asp Arg Lys Pro Lys Ala Glu Glu
                565                 570                 575
Asp Glu Ile Leu Asn Arg Ser Pro Arg Asn Arg Lys Pro Arg Arg Glu
            580                 585                 590

<210> SEQ ID NO 8
<211> LENGTH: 654
<212> TYPE: PRT
<213> ORGANISM: Homo sapiens

<400> SEQUENCE: 8

Met Lys Leu Ser Leu Val Ala Ala Met Leu Leu Leu Ser Ala Ala
1               5                   10                  15
Arg Ala Glu Glu Glu Asp Lys Lys Glu Asp Val Gly Thr Val Val Gly
                20                  25                  30
Ile Asp Leu Gly Thr Thr Tyr Ser Cys Val Gly Val Phe Lys Asn Gly
            35                  40                  45
Arg Val Glu Ile Ile Ala Asn Asp Gln Gly Asn Arg Ile Thr Pro Ser
        50                  55                  60
```

-continued

```
Tyr Val Ala Phe Thr Pro Glu Gly Glu Arg Leu Ile Gly Asp Ala Ala
 65                  70                  75                  80

Lys Asn Gln Leu Thr Ser Asn Pro Glu Asn Thr Val Phe Asp Ala Lys
                 85                  90                  95

Arg Leu Ile Gly Arg Thr Trp Asn Asp Pro Ser Val Gln Gln Asp Ile
            100                 105                 110

Lys Phe Leu Pro Phe Lys Val Val Glu Lys Lys Thr Lys Pro Tyr Ile
        115                 120                 125

Gln Val Asp Ile Gly Gly Gln Thr Lys Thr Phe Ala Pro Glu Glu
    130                 135                 140

Ile Ser Ala Met Val Leu Thr Lys Met Lys Glu Thr Ala Glu Ala Tyr
145                 150                 155                 160

Leu Gly Lys Lys Val Thr His Ala Val Val Thr Val Pro Ala Tyr Phe
                165                 170                 175

Asn Asp Ala Gln Arg Gln Ala Thr Lys Asp Ala Gly Thr Ile Ala Gly
            180                 185                 190

Leu Asn Val Met Arg Ile Ile Asn Glu Pro Thr Ala Ala Ala Ile Ala
        195                 200                 205

Tyr Gly Leu Asp Lys Arg Glu Gly Glu Lys Asn Ile Leu Val Phe Asp
    210                 215                 220

Leu Gly Gly Gly Thr Phe Asp Val Ser Leu Leu Thr Ile Asp Asn Gly
225                 230                 235                 240

Val Phe Glu Val Val Ala Thr Asn Gly Asp Thr His Leu Gly Gly Glu
                245                 250                 255

Asp Phe Asp Gln Arg Val Met Glu His Phe Ile Lys Leu Tyr Lys Lys
            260                 265                 270

Lys Thr Gly Lys Asp Val Arg Lys Asp Asn Arg Ala Val Gln Lys Leu
        275                 280                 285

Arg Arg Glu Val Glu Lys Ala Lys Arg Ala Leu Ser Ser Gln His Gln
    290                 295                 300

Ala Arg Ile Glu Ile Glu Ser Phe Tyr Glu Gly Glu Asp Phe Ser Glu
305                 310                 315                 320

Thr Leu Thr Arg Ala Lys Phe Glu Glu Leu Asn Met Asp Leu Phe Arg
                325                 330                 335

Ser Thr Met Lys Pro Val Gln Lys Val Leu Glu Asp Ser Asp Leu Lys
            340                 345                 350

Lys Ser Asp Ile Asp Glu Ile Val Leu Val Gly Gly Ser Thr Arg Ile
        355                 360                 365

Pro Lys Ile Gln Gln Leu Val Lys Glu Phe Phe Asn Gly Lys Glu Pro
    370                 375                 380

Ser Arg Gly Ile Asn Pro Asp Glu Ala Val Ala Tyr Gly Ala Ala Val
385                 390                 395                 400

Gln Ala Gly Val Leu Ser Gly Asp Gln Asp Thr Gly Asp Leu Val Leu
                405                 410                 415

Leu Asp Val Cys Pro Leu Thr Leu Gly Ile Glu Thr Val Gly Gly Val
            420                 425                 430

Met Thr Lys Leu Ile Pro Arg Asn Thr Val Val Pro Thr Lys Lys Ser
        435                 440                 445

Gln Ile Phe Ser Thr Ala Ser Asp Asn Gln Pro Thr Val Thr Ile Lys
    450                 455                 460

Val Tyr Glu Gly Glu Arg Pro Leu Thr Lys Asp Asn His Leu Leu Gly
465                 470                 475                 480

Thr Phe Asp Leu Thr Gly Ile Pro Pro Ala Pro Arg Gly Val Pro Gln
```

```
                        485                 490                 495
Ile Glu Val Thr Phe Glu Ile Asp Val Asn Gly Ile Leu Arg Val Thr
                500                 505                 510

Ala Glu Asp Lys Gly Thr Gly Asn Lys Asn Lys Ile Thr Ile Thr Asn
            515                 520                 525

Asp Gln Asn Arg Leu Thr Pro Glu Glu Ile Glu Arg Met Val Asn Asp
        530                 535                 540

Ala Glu Lys Phe Ala Glu Asp Lys Lys Leu Lys Glu Arg Ile Asp
545                 550                 555                 560

Thr Arg Asn Glu Leu Glu Ser Tyr Ala Tyr Ser Leu Lys Asn Gln Ile
                565                 570                 575

Gly Asp Lys Glu Lys Leu Gly Gly Lys Leu Ser Ser Glu Asp Lys Glu
            580                 585                 590

Thr Met Glu Lys Ala Val Glu Glu Lys Ile Glu Trp Leu Glu Ser His
        595                 600                 605

Gln Asp Ala Asp Ile Glu Asp Phe Lys Ala Lys Lys Lys Glu Leu Glu
    610                 615                 620

Glu Ile Val Gln Pro Ile Ile Ser Lys Leu Tyr Gly Ser Ala Gly Pro
625                 630                 635                 640

Pro Pro Thr Gly Glu Glu Asp Thr Ala Glu Lys Asp Glu Leu
                645                 650

<210> SEQ ID NO 9
<211> LENGTH: 508
<212> TYPE: PRT
<213> ORGANISM: Homo sapiens

<400> SEQUENCE: 9

Met Leu Arg Arg Ala Leu Leu Cys Leu Ala Val Ala Ala Leu Val Arg
1               5                   10                  15

Ala Asp Ala Pro Glu Glu Glu Asp His Val Leu Val Leu Arg Lys Ser
            20                  25                  30

Asn Phe Ala Glu Ala Leu Ala Ala His Lys Tyr Leu Leu Val Glu Phe
        35                  40                  45

Tyr Ala Pro Trp Cys Gly His Cys Lys Ala Leu Ala Pro Glu Tyr Ala
    50                  55                  60

Lys Ala Ala Gly Lys Leu Lys Ala Glu Gly Ser Glu Ile Arg Leu Ala
65                  70                  75                  80

Lys Val Asp Ala Thr Glu Glu Ser Asp Leu Ala Gln Gln Tyr Gly Val
                85                  90                  95

Arg Gly Tyr Pro Thr Ile Lys Phe Phe Arg Asn Gly Asp Thr Ala Ser
            100                 105                 110

Pro Lys Glu Tyr Thr Ala Gly Arg Glu Ala Asp Asp Ile Val Asn Trp
        115                 120                 125

Leu Lys Lys Arg Thr Gly Pro Ala Ala Thr Thr Leu Pro Asp Gly Ala
    130                 135                 140

Ala Ala Glu Ser Leu Val Glu Ser Ser Glu Val Ala Val Ile Gly Phe
145                 150                 155                 160

Phe Lys Asp Val Glu Ser Asp Ser Ala Lys Gln Phe Leu Gln Ala Ala
                165                 170                 175

Glu Ala Ile Asp Asp Ile Pro Phe Gly Ile Thr Ser Asn Ser Asp Val
            180                 185                 190

Phe Ser Lys Tyr Gln Leu Asp Lys Asp Gly Val Val Leu Phe Lys Lys
        195                 200                 205
```

```
Phe Asp Glu Gly Arg Asn Asn Phe Glu Gly Glu Val Thr Lys Glu Asn
    210                 215                 220
Leu Leu Asp Phe Ile Lys His Asn Gln Leu Pro Leu Val Ile Glu Phe
225                 230                 235                 240
Thr Glu Gln Thr Ala Pro Lys Ile Phe Gly Glu Ile Lys Thr His
                245                 250                 255
Ile Leu Leu Phe Leu Pro Lys Ser Val Ser Asp Tyr Asp Gly Lys Leu
                260                 265                 270
Ser Asn Phe Lys Thr Ala Ala Glu Ser Phe Lys Gly Lys Ile Leu Phe
            275                 280                 285
Ile Phe Ile Asp Ser Asp His Thr Asp Asn Gln Arg Ile Leu Glu Phe
        290                 295                 300
Phe Gly Leu Lys Lys Glu Glu Cys Pro Ala Val Arg Leu Ile Thr Leu
305                 310                 315                 320
Glu Glu Glu Met Thr Lys Tyr Lys Pro Glu Ser Glu Glu Leu Thr Ala
                325                 330                 335
Glu Arg Ile Thr Glu Phe Cys His Arg Phe Leu Glu Gly Lys Ile Lys
            340                 345                 350
Pro His Leu Met Ser Gln Glu Leu Pro Glu Asp Trp Asp Lys Gln Pro
        355                 360                 365
Val Lys Val Leu Val Gly Lys Asn Phe Glu Asp Val Ala Phe Asp Glu
370                 375                 380
Lys Lys Asn Val Phe Val Glu Phe Tyr Ala Pro Trp Cys Gly His Cys
385                 390                 395                 400
Lys Gln Leu Ala Pro Ile Trp Asp Lys Leu Gly Glu Thr Tyr Lys Asp
                405                 410                 415
His Glu Asn Ile Val Ile Ala Lys Met Asp Ser Thr Ala Asn Glu Val
            420                 425                 430
Glu Ala Val Lys Val His Ser Phe Pro Thr Leu Lys Phe Phe Pro Ala
        435                 440                 445
Ser Ala Asp Arg Thr Val Ile Asp Tyr Asn Gly Glu Arg Thr Leu Asp
450                 455                 460
Gly Phe Lys Lys Phe Leu Glu Ser Gly Gly Gln Asp Gly Ala Gly Asp
465                 470                 475                 480
Asp Asp Asp Leu Glu Asp Leu Glu Glu Ala Glu Glu Pro Asp Met Glu
                485                 490                 495
Glu Asp Asp Asp Gln Lys Ala Val Lys Asp Glu Leu
            500                 505

<210> SEQ ID NO 10
<211> LENGTH: 602
<212> TYPE: PRT
<213> ORGANISM: Homo sapiens

<400> SEQUENCE: 10

Met Pro Ser Ala Lys Gln Arg Gly Ser Lys Gly His Gly Ala Ala
1               5                   10                  15
Ser Pro Ser Glu Lys Gly Ala His Pro Ser Gly Ala Asp Asp Val
            20                  25                  30
Ala Lys Lys Pro Pro Ala Pro Gln Gln Pro Pro Pro Pro Ala
        35                  40                  45
Pro His Pro Gln Gln His Pro Gln Gln His Pro Gln Asn Gln Ala His
    50                  55                  60
Gly Lys Gly Gly His Arg Gly Gly Gly Gly Gly Lys Ser Ser
65                  70                  75                  80
```

-continued

```
Ser Ser Ser Ser Ala Ser Ala Ala Ala Ala Ala Ala Ala Ser Ser
            85                  90                  95

Ser Ala Ser Cys Ser Arg Arg Leu Gly Arg Ala Leu Asn Phe Leu Phe
            100                 105                 110

Tyr Leu Ala Leu Val Ala Ala Ala Phe Ser Gly Trp Cys Val His
            115                 120                 125

His Val Leu Glu Glu Val Gln Gln Val Arg Arg Ser His Gln Asp Phe
    130                 135                 140

Ser Arg Gln Arg Glu Glu Leu Gly Gln Gly Leu Gln Gly Val Glu Gln
145                 150                 155                 160

Lys Val Gln Ser Leu Gln Ala Thr Phe Gly Thr Phe Glu Ser Ile Leu
                165                 170                 175

Arg Ser Ser Gln His Lys Gln Asp Leu Thr Glu Lys Ala Val Lys Gln
                180                 185                 190

Gly Glu Ser Glu Val Ser Arg Ile Ser Glu Val Leu Gln Lys Leu Gln
            195                 200                 205

Asn Glu Ile Leu Lys Asp Leu Ser Asp Gly Ile His Val Val Lys Asp
    210                 215                 220

Ala Arg Glu Arg Asp Phe Thr Ser Leu Glu Asn Thr Val Glu Glu Arg
225                 230                 235                 240

Leu Thr Glu Leu Thr Lys Ser Ile Asn Asp Asn Ile Ala Ile Phe Thr
                245                 250                 255

Glu Val Gln Lys Arg Ser Gln Lys Glu Ile Asn Asp Met Lys Ala Lys
            260                 265                 270

Val Ala Ser Leu Glu Glu Ser Glu Gly Asn Lys Gln Asp Leu Lys Ala
            275                 280                 285

Leu Lys Glu Ala Val Lys Glu Ile Gln Thr Ser Ala Lys Ser Arg Glu
    290                 295                 300

Trp Asp Met Glu Ala Leu Arg Ser Thr Leu Gln Thr Met Glu Ser Asp
305                 310                 315                 320

Ile Tyr Thr Glu Val Arg Glu Leu Val Ser Leu Lys Gln Glu Gln Gln
                325                 330                 335

Ala Phe Lys Glu Ala Ala Asp Thr Glu Arg Leu Ala Leu Gln Ala Leu
            340                 345                 350

Thr Glu Lys Leu Leu Arg Ser Glu Glu Ser Val Ser Arg Leu Pro Glu
            355                 360                 365

Glu Ile Arg Arg Leu Glu Glu Glu Leu Arg Gln Leu Lys Ser Asp Ser
    370                 375                 380

His Gly Pro Lys Glu Asp Gly Gly Phe Arg His Ser Glu Ala Phe Glu
385                 390                 395                 400

Ala Leu Gln Gln Lys Ser Gln Gly Leu Asp Ser Arg Leu Gln His Val
                405                 410                 415

Glu Asp Gly Val Leu Ser Met Gln Val Ala Ser Ala Arg Gln Thr Glu
            420                 425                 430

Ser Leu Glu Ser Leu Leu Ser Lys Ser Gln Glu His Glu Gln Arg Leu
            435                 440                 445

Ala Ala Leu Gln Gly Arg Leu Glu Gly Leu Gly Ser Ser Glu Ala Asp
    450                 455                 460

Gln Asp Gly Leu Ala Ser Thr Val Arg Ser Leu Gly Glu Thr Gln Leu
465                 470                 475                 480

Val Leu Tyr Gly Asp Val Glu Glu Leu Lys Arg Ser Val Gly Glu Leu
                485                 490                 495
```

```
Pro Ser Thr Val Glu Ser Leu Gln Lys Val Gln Glu Gln Val His Thr
            500                 505                 510
Leu Leu Ser Gln Asp Gln Ala Gln Ala Ala Arg Leu Pro Pro Gln Asp
        515                 520                 525
Phe Leu Asp Arg Leu Ser Ser Leu Asp Asn Leu Lys Ala Ser Val Ser
    530                 535                 540
Gln Val Glu Ala Asp Leu Lys Met Leu Arg Thr Ala Val Asp Ser Leu
545                 550                 555                 560
Val Ala Tyr Ser Val Lys Ile Glu Thr Asn Glu Asn Leu Glu Ser
                565                 570                 575
Ala Lys Gly Leu Leu Asp Asp Leu Arg Asn Asp Leu Asp Arg Leu Phe
                580                 585                 590
Val Lys Val Glu Lys Ile His Glu Lys Val
                595                 600

<210> SEQ ID NO 11
<211> LENGTH: 876
<212> TYPE: PRT
<213> ORGANISM: Homo sapiens

<400> SEQUENCE: 11

Met Glu Leu Ile Thr Ile Leu Glu Lys Thr Val Ser Pro Asp Arg Leu
1               5                   10                  15
Glu Leu Glu Ala Ala Gln Lys Phe Leu Glu Arg Ala Ala Val Glu Asn
            20                  25                  30
Leu Pro Thr Phe Leu Val Glu Leu Ser Arg Val Leu Ala Asn Pro Gly
        35                  40                  45
Asn Ser Gln Val Ala Arg Val Ala Ala Gly Leu Gln Ile Lys Asn Ser
    50                  55                  60
Leu Thr Ser Lys Asp Pro Asp Ile Lys Ala Gln Tyr Gln Gln Arg Trp
65                  70                  75                  80
Leu Ala Ile Asp Ala Asn Ala Arg Arg Glu Val Lys Asn Tyr Val Leu
                85                  90                  95
Gln Thr Leu Gly Thr Glu Thr Tyr Arg Pro Ser Ser Ala Ser Gln Cys
            100                 105                 110
Val Ala Gly Ile Ala Cys Ala Glu Ile Pro Val Asn Gln Trp Pro Glu
        115                 120                 125
Leu Ile Pro Gln Leu Val Ala Asn Val Thr Asn Pro Asn Ser Thr Glu
    130                 135                 140
His Met Lys Glu Ser Thr Leu Glu Ala Ile Gly Tyr Ile Cys Gln Asp
145                 150                 155                 160
Ile Asp Pro Glu Gln Leu Gln Asp Lys Ser Asn Glu Ile Leu Thr Ala
                165                 170                 175
Ile Ile Gln Gly Met Arg Lys Glu Glu Pro Ser Asn Asn Val Lys Leu
            180                 185                 190
Ala Ala Thr Asn Ala Leu Leu Asn Ser Leu Glu Phe Thr Lys Ala Asn
        195                 200                 205
Phe Asp Lys Glu Ser Glu Arg His Phe Ile Met Gln Val Val Cys Glu
    210                 215                 220
Ala Thr Gln Cys Pro Asp Thr Arg Val Arg Val Ala Ala Leu Gln Asn
225                 230                 235                 240
Leu Val Lys Ile Met Ser Leu Tyr Tyr Gln Tyr Met Glu Thr Tyr Met
                245                 250                 255
Gly Pro Ala Leu Phe Ala Ile Thr Ile Glu Ala Met Lys Ser Asp Ile
            260                 265                 270
```

-continued

```
Asp Glu Val Ala Leu Gln Gly Ile Glu Phe Trp Ser Asn Val Cys Asp
            275                 280                 285
Glu Glu Met Asp Leu Ala Ile Glu Ala Ser Glu Ala Ala Glu Gln Gly
        290                 295                 300
Arg Pro Pro Glu His Thr Ser Lys Phe Tyr Ala Lys Gly Ala Leu Gln
305                 310                 315                 320
Tyr Leu Val Pro Ile Leu Thr Gln Thr Leu Thr Lys Gln Asp Glu Asn
                325                 330                 335
Asp Asp Asp Asp Asp Trp Asn Pro Cys Lys Ala Ala Gly Val Cys Leu
            340                 345                 350
Met Leu Leu Ala Thr Cys Cys Glu Asp Ile Val Pro His Val Leu
        355                 360                 365
Pro Phe Ile Lys Glu His Ile Lys Asn Pro Asp Trp Arg Tyr Arg Asp
370                 375                 380
Ala Ala Val Met Ala Phe Gly Cys Ile Leu Glu Gly Pro Glu Pro Ser
385                 390                 395                 400
Gln Leu Lys Pro Leu Val Ile Gln Ala Met Pro Thr Leu Ile Glu Leu
                405                 410                 415
Met Lys Asp Pro Ser Val Val Val Arg Asp Thr Ala Ala Trp Thr Val
            420                 425                 430
Gly Arg Ile Cys Glu Leu Leu Pro Glu Ala Ala Ile Asn Asp Val Tyr
        435                 440                 445
Leu Ala Pro Leu Leu Gln Cys Leu Ile Glu Gly Leu Ser Ala Glu Pro
450                 455                 460
Arg Val Ala Ser Asn Val Cys Trp Ala Phe Ser Ser Leu Ala Glu Ala
465                 470                 475                 480
Ala Tyr Glu Ala Ala Asp Val Ala Asp Gln Glu Glu Pro Ala Thr
                485                 490                 495
Tyr Cys Leu Ser Ser Ser Phe Glu Leu Ile Val Gln Lys Leu Leu Glu
            500                 505                 510
Thr Thr Asp Arg Pro Asp Gly His Gln Asn Asn Leu Arg Ser Ser Ala
        515                 520                 525
Tyr Glu Ser Leu Met Glu Ile Val Lys Asn Ser Ala Lys Asp Cys Tyr
530                 535                 540
Pro Ala Val Gln Lys Thr Thr Leu Val Ile Met Glu Arg Leu Gln Gln
545                 550                 555                 560
Val Leu Gln Met Glu Ser His Ile Gln Ser Thr Ser Asp Arg Ile Gln
                565                 570                 575
Phe Asn Asp Leu Gln Ser Leu Leu Cys Ala Thr Leu Gln Asn Val Leu
            580                 585                 590
Arg Lys Val Gln His Gln Asp Ala Leu Gln Ile Ser Asp Val Val Met
        595                 600                 605
Ala Ser Leu Leu Arg Met Phe Gln Ser Thr Ala Gly Ser Gly Val
610                 615                 620
Gln Glu Asp Ala Leu Met Ala Val Ser Thr Leu Val Glu Val Leu Gly
625                 630                 635                 640
Gly Glu Phe Leu Lys Tyr Met Glu Ala Phe Lys Pro Phe Leu Gly Ile
                645                 650                 655
Gly Leu Lys Asn Tyr Ala Glu Tyr Gln Val Cys Leu Ala Ala Val Gly
            660                 665                 670
Leu Val Gly Asp Leu Cys Arg Ala Leu Gln Ser Asn Ile Ile Pro Phe
        675                 680                 685
```

```
Cys Asp Glu Val Met Gln Leu Leu Leu Glu Asn Leu Gly Asn Glu Asn
690                 695                 700

Val His Arg Ser Val Lys Pro Gln Ile Leu Ser Val Phe Gly Asp Ile
705                 710                 715                 720

Ala Leu Ala Ile Gly Gly Glu Phe Lys Lys Tyr Leu Glu Val Val Leu
                725                 730                 735

Asn Thr Leu Gln Gln Ala Ser Gln Ala Gln Val Asp Lys Ser Asp Tyr
            740                 745                 750

Asp Met Val Asp Tyr Leu Asn Glu Leu Arg Glu Ser Cys Leu Glu Ala
        755                 760                 765

Tyr Thr Gly Ile Val Gln Gly Leu Lys Gly Asp Gln Glu Asn Val His
    770                 775                 780

Pro Asp Val Met Leu Val Gln Pro Arg Val Glu Phe Ile Leu Ser Phe
785                 790                 795                 800

Ile Asp His Ile Ala Gly Asp Glu Asp His Thr Asp Gly Val Val Ala
                805                 810                 815

Cys Ala Ala Gly Leu Ile Gly Asp Leu Cys Thr Ala Phe Gly Lys Asp
                820                 825                 830

Val Leu Lys Leu Val Glu Ala Arg Pro Met Ile His Glu Leu Leu Thr
            835                 840                 845

Glu Gly Arg Arg Ser Lys Thr Asn Lys Ala Lys Thr Leu Ala Thr Trp
850                 855                 860

Ala Thr Lys Glu Leu Arg Lys Leu Lys Asn Gln Ala
865                 870                 875

<210> SEQ ID NO 12
<211> LENGTH: 216
<212> TYPE: PRT
<213> ORGANISM: Homo sapiens

<400> SEQUENCE: 12

Met Ala Ala Gln Gly Glu Pro Gln Val Gln Phe Lys Leu Val Leu Val
1               5                   10                  15

Gly Asp Gly Gly Thr Gly Lys Thr Thr Phe Val Lys Arg His Leu Thr
            20                  25                  30

Gly Glu Phe Glu Lys Lys Tyr Val Ala Thr Leu Gly Val Glu Val His
        35                  40                  45

Pro Leu Val Phe His Thr Asn Arg Gly Pro Ile Lys Phe Asn Val Trp
50                  55                  60

Asp Thr Ala Gly Gln Glu Lys Phe Gly Gly Leu Arg Asp Gly Tyr Tyr
65                  70                  75                  80

Ile Gln Ala Gln Cys Ala Ile Ile Met Phe Asp Val Thr Ser Arg Val
                85                  90                  95

Thr Tyr Lys Asn Val Pro Asn Trp His Arg Asp Leu Val Arg Val Cys
            100                 105                 110

Glu Asn Ile Pro Ile Val Leu Cys Gly Asn Lys Val Asp Ile Lys Asp
        115                 120                 125

Arg Lys Val Lys Ala Lys Ser Ile Val Phe His Arg Lys Lys Asn Leu
    130                 135                 140

Gln Tyr Tyr Asp Ile Ser Ala Lys Ser Asn Tyr Asn Phe Glu Lys Pro
145                 150                 155                 160

Phe Leu Trp Leu Ala Arg Lys Leu Ile Gly Asp Pro Asn Leu Glu Phe
                165                 170                 175

Val Ala Met Pro Ala Leu Ala Pro Pro Glu Val Val Met Asp Pro Ala
            180                 185                 190
```

-continued

```
Leu Ala Ala Gln Tyr Glu His Asp Leu Glu Val Ala Gln Thr Thr Ala
        195                 200                 205

Leu Pro Asp Glu Asp Asp Leu
    210             215

<210> SEQ ID NO 13
<211> LENGTH: 451
<212> TYPE: PRT
<213> ORGANISM: Homo sapiens

<400> SEQUENCE: 13

Met Pro Arg Glu Ile Ile Thr Leu Gln Leu Gly Gln Cys Gly Asn Gln
1               5                   10                  15

Ile Gly Phe Glu Phe Trp Lys Gln Leu Cys Ala Glu His Gly Ile Ser
            20                  25                  30

Pro Glu Gly Ile Val Glu Glu Phe Ala Thr Glu Gly Thr Asp Arg Lys
        35                  40                  45

Asp Val Phe Phe Tyr Gln Ala Asp Asp Glu His Tyr Ile Pro Arg Ala
    50                  55                  60

Val Leu Leu Asp Leu Glu Pro Arg Val Ile His Ser Ile Leu Asn Ser
65                  70                  75                  80

Pro Tyr Ala Lys Leu Tyr Asn Pro Glu Asn Ile Tyr Leu Ser Glu His
                85                  90                  95

Gly Gly Gly Ala Gly Asn Asn Trp Ala Ser Gly Phe Ser Gln Gly Glu
            100                 105                 110

Lys Ile His Glu Asp Ile Phe Asp Ile Ile Asp Arg Glu Ala Asp Gly
        115                 120                 125

Ser Asp Ser Leu Glu Gly Phe Val Leu Cys His Ser Ile Ala Gly Gly
    130                 135                 140

Thr Gly Ser Gly Leu Gly Ser Tyr Leu Leu Glu Arg Leu Asn Asp Arg
145                 150                 155                 160

Tyr Pro Lys Lys Leu Val Gln Thr Tyr Ser Val Phe Pro Tyr Gln Asp
                165                 170                 175

Glu Met Ser Asp Val Val Val Gln Pro Tyr Asn Ser Leu Leu Thr Leu
            180                 185                 190

Lys Arg Leu Thr Gln Asn Ala Asp Cys Val Val Leu Asp Asn Thr
        195                 200                 205

Ala Leu Asn Arg Ile Ala Thr Asp Arg Leu His Ile Gln Asn Pro Ser
    210                 215                 220

Phe Ser Gln Ile Asn Gln Leu Val Ser Thr Ile Met Ser Ala Ser Thr
225                 230                 235                 240

Thr Thr Leu Arg Tyr Pro Gly Tyr Met Asn Asn Asp Leu Ile Gly Leu
                245                 250                 255

Ile Ala Ser Leu Ile Pro Thr Pro Arg Leu His Phe Leu Met Thr Gly
            260                 265                 270

Tyr Thr Pro Leu Thr Thr Asp Gln Ser Val Ala Ser Val Arg Lys Thr
        275                 280                 285

Thr Val Leu Asp Val Met Arg Arg Leu Leu Gln Pro Lys Asn Val Met
    290                 295                 300

Val Ser Thr Gly Arg Asp Arg Gln Thr Asn His Cys Tyr Ile Ala Ile
305                 310                 315                 320

Leu Asn Ile Ile Gln Gly Glu Val Asp Pro Thr Gln Val His Lys Ser
                325                 330                 335

Leu Gln Arg Ile Arg Glu Arg Lys Leu Ala Asn Phe Ile Pro Trp Gly
```

-continued

```
                340                 345                 350
Pro Ala Ser Ile Gln Val Ala Leu Ser Arg Lys Ser Pro Tyr Leu Pro
        355                 360                 365

Ser Ala His Arg Val Ser Gly Leu Met Met Ala Asn His Thr Ser Ile
    370                 375                 380

Ser Ser Leu Phe Glu Ser Ser Cys Gln Gln Phe Asp Lys Leu Arg Lys
385                 390                 395                 400

Arg Asp Ala Phe Leu Glu Gln Phe Arg Lys Glu Asp Met Phe Lys Asp
            405                 410                 415

Asn Phe Asp Glu Met Asp Arg Ser Arg Glu Val Val Gln Glu Leu Ile
            420                 425                 430

Asp Glu Tyr His Ala Ala Thr Gln Pro Asp Tyr Ile Ser Trp Gly Thr
        435                 440                 445

Gln Glu Gln
    450
```

DETECTION OF THE NUCLEOLAR CHANNEL SYSTEM OF HUMAN ENDOMETRIUM AND USES THEREOF

CROSS-REFERENCE TO RELATED APPLICATION

This application claims the benefit of U.S. Provisional Patent Application No. 61/062,827, filed on Jan. 29, 2008, the content of which is hereby incorporated by reference.

FIELD OF THE INVENTION

The present invention generally relates to methods for assaying at the light microscopic level for the presence or absence of nucleolar channel systems (NCSs) in an endometrial tissue sample; methods for determining whether or not a postovulatory human endometrium is in a state that is receptive for implantation of a human embryo, where the presence of NCSs indicates that the endometrium is in a state that is receptive for implantation of an embryo and the absence of NCSs indicates that the endometrium is not in a state that is receptive for implantation of the embryo; and methods for determining the effectiveness of a contraceptive in a woman, comprising assaying an endometrial tissue sample for the presence or absence of NCSs.

BACKGROUND OF THE INVENTION

Throughout this application various publications are referred to in parenthesis. Citations for these references may be found at the end of the specification immediately preceding the claims. The disclosures of these publications are hereby incorporated by reference in their entireties into the subject application to more fully describe the art to which the subject application pertains.

During an idealized 28-day human menstrual cycle, the endometrium undergoes well-timed changes in preparation for embryo implantation. The follicular or proliferative phase is separated by ovulation on day 14 from the luteal or secretory phase. The endometrium is only receptive for a short two-day period during luteal days 20-24 (Wilcox et al., 1999). Inaccurate identification of this implantation window is a major cause for the low success rate in artificial reproductive technologies (Norwitz et al., 2001).

These temporal changes of the endometrium are evident on the tissue and epithelial cell level. In fact, histological changes have been the gold standard for endometrial dating for the past 50 years but their value has recently been questioned (Coutifaris et al., 2004; Murray et al., 2004; Noyes et al., 1950). Among the ultrastructural hallmarks of endometrial epithelial cells are giant mitochondria, subnuclear glycogen deposits, pinopodes, and nucleolar channel systems (NCSs) (Martel, 1981; Spornitz, 1992). Whereas giant mitochondria and subnuclear glycogen deposits appear in the early luteal phase, pinopodes and NCSs more closely overlap with the mid luteal window of implantation and could serve as potential markers (Clyman, 1963; Nikas et al, 1995).

NCSs were discovered in the nuclei of endometrial epithelial cells using transmission electron microscopy, which is still their only method of identification (Dubrauszky and Pohlmann, 1960). NCSs are small globular structures of about 1 μm in diameter and consist of three components, intertwined membrane tubules embedded in an electron dense matrix, and an amorphous core that is separated from the nucleoplasm by the tubules and matrix (Clyman, 1963; Moricard and Moricard, 1964; Terzakis, 1965). Using histochemical labeling, the activity of glucose-6-phosphatase, a marker enzyme of endoplasmic reticulum, was documented in the lumen of the membrane tubules indicating their derivation from this cytoplasmic organelle, apparently through the contiguous nuclear envelope (Kittur et al., 2007).

Understanding of nuclear structure and function has advanced significantly (Stewart et al., 2007; Terry et al., 2007; Trinkle-Mulcahy and Lamond, 2007). Nuclear pore complexes (NPCs) perforate the nuclear envelope at the sites where the outer and inner nuclear membranes fuse and are thought to serve as the sole portal between nucleus and cytoplasm. The NPCs are large complex protein assemblies consisting of 35 or so proteins (nucleoporins) present in multiple copies and arranged in partial symmetry across the envelope and around the pore. Although some nucleoporins can exchange off NPCs during interphase and some concentrate in kinetochores during mitosis when NPCs disassemble, they are generally restricted to intact NPCs (Belgareh et al., 2001; Rabut et al., 2004). Whereas the outer membrane and the perinuclear space mirror the proteins of the attached endoplasmic reticulum, the protein composition of the inner nuclear membrane is distinct. Inner membrane proteins anchor the lamina (an intermediate filament meshwork lining the nucleoplasmic side) and/or chromatin at the nuclear envelope. Several of these proteins, including lamins (proteins of the lamina), are mutated in inherited diseases ranging from muscular dystrophies to progeria (premature aging) (Stewart et al., 2007).

Several lines of evidence suggest a role for NCSs in the preparation of the endometrium for reception of the embryo. NCSs have strictly been observed post ovulation, only on cycle days 16-24, and are not detected in pregnancy (Clyman, 1963). They appear to be induced by progesterone and are sensitive to oral and intrauterine contraceptives (Azadian-Boulanger et al., 1976; Feria-Velasco et al., 1972; Kohorn et al., 1970; Kohorn et al., 1972; Pryse-Davies et al., 1979; Roberts et al., 1975; Wynn, 1967). Finally, in several cases of unexplained infertility the absence or delayed appearance of NCSs was noted as the sole abnormal endometrial parameter (Dockery et al., 1996; Gore and Gordon, 1974; Kohorn et al., 1972). Despite this and additional evidence, NCSs have been neglected as potential markers or prerequisites for implantation. This can be mostly attributed to difficulty of their detection requiring transmission electron microscopy, which is further complicated by their small size and the perception that only about 5% of all endometrial epithelial cells develop NCSs (Novotny et al., 1999; Ryder et al., 1995). Accordingly, a method is needed that can be readily used to mark the window of uterine receptivity.

SUMMARY OF THE INVENTION

The present invention is directed to methods of assaying for the presence or absence of nucleolar channel systems (NCSs) in an endometrial tissue sample, where the methods comprise contacting the tissue sample with an agent that is specific for a protein selected from the group consisting of one or more of Nup153, Nup62, Tpr, Lamin A/C, Lamin A, Lamin B2, Emerin, Calnexin, BiP, PDI, CLIMP63, Karyopherin beta 1, Ran and gamma-tubulin, wherein the presence of the protein within nuclei of endometrial epithelial cells indicates the presence of NCSs in the endometrial tissue sample and wherein the absence of the protein within nuclei of endometrial epithelial cells indicates the absence of NCSs in the endometrial tissue sample.

The invention also provides methods of determining whether or not a postovulatory human endometrium is in a state that is receptive for implantation of a human embryo, where the methods comprise contacting a tissue sample from the endometrium with an agent that binds to nucleolar channel systems (NCSs), wherein the presence of NCSs indicates that the endometrium is in a state that is receptive for implantation of an embryo and the absence of NCSs indicates that the endometrium is not in a state that is receptive for implantation of an embryo.

The invention further provides methods of determining the effectiveness of a contraceptive in a woman, where the methods comprise contacting a tissue sample from the endometrium of a woman who is taking the contraceptive with an agent that binds to nucleolar channel systems (NCSs), wherein the presence of NCSs indicates that the contraceptive may not be effective and wherein the absence of NCSs between day 18 and day 24 of a 28 day menstrual cycle and/or between day 4 and day 9 of the luteal phase of the menstrual cycle indicates that the contraceptive is effective, where day 1 of the cycle is defined as the first day of menstrual blood loss.

BRIEF DESCRIPTION OF THE DRAWINGS

FIG. 1-1C'. The monoclonal antibody 414 (mAb414) directed against nuclear pore complex (NPC) proteins exhibits a strong preference for NCSs. (A) Double fluorescence of mAb414 (A) and DAPI DNA stain (A") on a semi-thin frozen section of human endometrium in the secretory phase. NCS fluorescence appears as rings (A, arrows). The rings, i.e., the matrix and membrane tubules of NCSs, appear as phase dense circles in phase contrast microscopy (A', arrows). Moreover, NCSs are often encircled by nucleoli (arrowheads) and, like nucleoli, appear chromatin-free (A"). The concentration of mAb414 antigens in NCSs is so high that the classical rim staining of NPCs only becomes visible if the image is overexposed to an extent that saturates NCS staining (A'"). Bar=5 μm. (B) MAb414 immunogold-stained electron micrograph of an ultrathin cryosection of luteal human endometrium. Note the strong and specific gold labeling of a grazing section of a NCS (i.e., its core is covered by its membrane tubules and matrix) that is embedded in a nucleolus (No) and attached to the nuclear envelope (NE). At least one NPC of a neighboring cell is identified by mAb414 (arrow). Bar=0.5 μm. (C) Confocal micrograph of indirect mAb414 fluorescence of a 7 μm-thick paraffin section of luteal human endometrium. In a single 0.2 μm optical section a NCS is visible in only one of the nuclei defined by the classical rim staining of NPCs (C), whereas, in a maximum projection of all optical planes, all nuclei outlined by hazy NPC staining contain NCSs (C'). Bar=5 μm.

DETAILED DESCRIPTION OF THE INVENTION

Figures 1A, 1B, 1C:
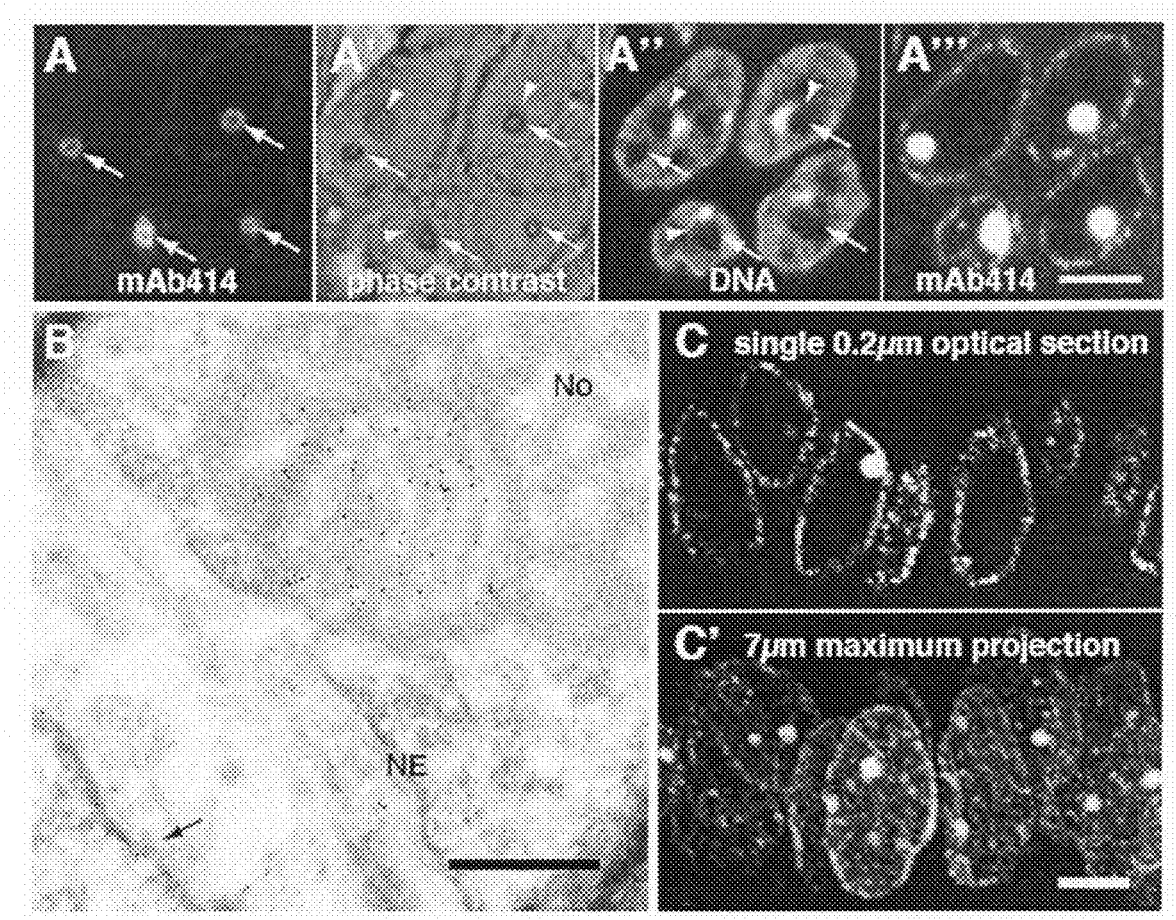

The invention is directed to a method of assaying for the presence or absence of nucleolar channel systems (NCSs) in an endometrial tissue sample, where the method comprises contacting the tissue sample with an agent that is specific for a protein selected from the group consisting of one or more of Nup153, Nup62, Tpr, Lamin A/C, Lamin A, Lamin B2, Emerin, Calnexin, BiP, PDI, CLIMP63, Karyopherin beta 1, Ran and gamma-tubulin, wherein the presence of the protein within nuclei of endometrial epithelial cells indicates the presence of NCSs in the endometrial tissue sample and wherein the absence of the protein within nuclei of endometrial epithelial cells indicates the absence of NCSs in the endometrial tissue sample. The presence of NCSs indicates that the endometrium is in a state that is receptive for implantation of an embryo. Where the tissue sample is obtained from the endometrium of a woman between day 18 and day 24, and more preferably between day 19 and day 22, of a 28 day menstrual cycle, where day 1 of the cycle is defined as the first day of menstrual blood loss, the absence of NCSs indicates that the endometrium is not in a state that is receptive for implantation of an embryo. Similarly, where the tissue sample is obtained from the endometrium of a woman between between day 4 and day 9 of the luteal phase of the menstrual cycle, and more preferably between day 5 and day 8 of the luteal phase, the absence of NCSs indicates that the endometrium is not in a state that is receptive for implantation of an embryo. The luteal phase can be determined based on detection of the luteinizing hormone (LH) surge in the urine, which marks luteal day 0 (equivalent to day 14 of a 28 day menstrual cycle).

The invention also provides a method of determining whether or not a postovulatory human endometrium is in a state that is receptive for implantation of a human embryo, the method comprising contacting a tissue sample from the endometrium with an agent that binds to nucleolar channel systems (NCSs), wherein the presence of NCSs indicates that the endometrium is in a state that is receptive for implantation of an embryo and the absence of NCSs indicates that the endometrium is not in a state that is receptive for implantation of an embryo. Preferably, the tissue sample is obtained from the endometrium of a woman between day 18 and day 24 of a 28 day menstrual cycle, where day 1 of the cycle is defined as the first day of menstrual blood loss. More preferably, the tissue sample is obtained from the endometrium of a woman between day 19 and day 22 of a 28 day menstrual cycle. Preferably, the tissue sample is obtained from the endometrium of a woman between day 4 and day 9 of the luteal phase of the menstrual cycle, and more preferably between day 5 and day 8 of the luteal phase of the menstrual cycle.

The invention further provides a method of determining the effectiveness of a contraceptive in a woman, the method comprising contacting a tissue sample from the endometrium of a woman who is taking the contraceptive with an agent that binds to nucleolar channel systems (NCSs), wherein the presence of NCSs indicates that the contraceptive may not be effective and wherein the absence of NCSs between day 18 and day 24 of a 28 day menstrual cycle and/or between day 4 and day 9 of the luteal phase of the menstrual cycle indicates that the contraceptive is effective, where day 1 of the cycle is defined as the first day of menstrual blood loss. Preferably, the absence of NCSs between day 19 and day 22 of a 28 day menstrual cycle and/or between day 5 and day 8 of the luteal phase of the menstrual cycle indicates that the contraceptive is effective.

NCSs can be assayed using an agent that binds NCSs such as, for example, an antibody, an antibody fragment, a peptide, a lectin or an aptamer. As used herein, the term "antibody fragment" means fragments of whole antibodies wherein the fragments bind to NCSs. Antibody fragments include, but are not limited to, F(ab')$_2$ and Fab' fragments and single chain antibodies. F(ab')$_2$ is an antigen binding fragment of an antibody molecule with deleted crystallizable fragment (Fc) region and preserved binding region. Fab' is ½ of the F(ab')$_2$ molecule possessing only ½ of the binding region. The term antibody is further meant to encompass polyclonal antibodies and monoclonal antibodies. Antibodies may be produced by techniques well known to those skilled in the art. The antibody can be, e.g., any of an IgA, IgD, IgE, IgG, or IgM antibody. Aptamers are single stranded oligonucleotides or oligonucleotide analogs that bind to a particular target molecule, such as a protein. Thus, aptamers are the oligonucleotide analogy to antibodies. Both RNA and single stranded DNA (or analog) aptamers can be used.

The agent that binds to NCSs can be labeled with a detectable marker. Labeling may be accomplished using one of a variety of labeling techniques, including peroxidase, chemiluminescent, and/or radioactive labels known in the art. The detectable marker may be, for example, a nonradioactive or fluorescent marker, such as biotin, fluorescein (FITC), acridine, cholesterol, or carboxy-X-rhodamine, which can be detected using fluorescence and other imaging techniques readily known in the art. Alternatively, the detectable marker may be a radioactive marker, including, for example, a radioisotope. The radioisotope may be any isotope that emits detectable radiation, such as, for example, $^{35}$S, $^{32}$P, or $^3$H. Radioactivity emitted by the radioisotope can be detected by techniques well known in the art. For example, gamma emission from the radioisotope may be detected using gamma imaging techniques, particularly scintigraphic imaging.

The agent, for example, can be specific for a protein selected from the group consisting of, but not limited to, one or more of Nup153, Nup62, Tpr, Lamin A/C, Lamin A, Lamin B2, Emerin, Calnexin, BiP, PDI, CLIMP63, Karyopherin beta 1, Ran and gamma-tubulin. Preferably, the agent is specific for a protein selected from the group consisting of one or more of Nup153, Lamin A/C and Emerin. A preferred agent is monoclonal antibody 414 (MAb414), which is commercially available from Covance, Berkely, Calif. The presence or absence of the protein, and the presence or absence of NCSs, can be determined using a light microscope.

The methods of the present invention can also be carried using a combination of agents that detect a plurality of Nup153, Nup62, Tpr, Lamin A/C, Lamin A, Lamin B2, Emerin, Calnexin, BiP, PDI, CLIMP63, Karyopherin beta 1, Ran and gamma-tubulin. For example, two or more agents can be used, where each agent is specific for Nup153, Nup62, Tpr, Lamin A/C, Lamin A, Lamin B2, Emerin, Calnexin, BiP, PDI, CLIMP63, Karyopherin beta 1, Ran or gamma-tubulin.

Amino acid sequences for 13 preferred proteins are indicated below, where the standard single letter code is used for each amino acid.

```
Nup153 (human) Locus and Accession No. P49790
                                                          (SEQ ID NO: 1)
  1 masgaggvgg ggggkirtrr chqgpikpyq qgrqqhqgil srvtesvkni vpgwlqryfn 61 knedvcscst dtsevprwpe nkedhlvyad eessnitdgr itpepavsnt eepsttstas 121 nypdvltrps lhrshlnfsm lespalhcqp stssafpigs sgfslvkeik dstsqhdddn 181 isttsgfssr asdkditvsk ntslpplwsp eaershslsq htatsskkpa fnlsafgtls 241 pslgnssilk tsqlgdspfy pgkttyggaa aavrqsklrn tpyqapvrrq mkakqlsaqs 301 ygvtsstarr ilqslekmss pladakrips ivssplnspl drsgiditdf qakrekvdsq 361 yppvqrlmtp kpvsiatnrs vyfkpsltps gefrktnqri dnkcstgyek nmtpgqnreq 421 resgfsypnf slpaanglss gvqggggkmr rerhafvask pleeeemevp vlpkislpit 481 ssslptfnfs speittssps pinssqaltn kvqmtspsst gspmfkfssp ivksteanvl 541 ppssigftfs vpvaktaels gssstlepii sssahhvttv nstnckktpp edcegpfrpa 601 eilkegsvld ilkspgfasp kidsvaaqpt atspvvytrp aissfsssgi gfgeslkags
```

-continued

```
 661 swqcdtcllq nkvtdnkcia cqaaklsprd takqtgietp nksgkttlsa sgtgfgdkfk
 721 pvigtwdcdt clvqnkpeai kcvacetpkp gtcvkraltl tvvsesaetm tasssssctvt
 781 tgtlgfgdkf krpigswecs vccvsnnaed nkcvscmsek pgssvpasss stvpvslpsg
 841 gslglekfkk pegswdcelc lvqnkadstk clacesakpg tksgfkgfdt sssssnsaas
 901 ssfkfgvsss ssgpsqtlts tgnfkfgdqg gfkigvssds gsinpmsegf kfskpigdfk
 961 fgvsseskpe evkkdskndn fkfglssgls npvsltpfqf gvsnlgqeek keelpksssa
1021 gfsfgtgvin stpapantiv tsenkssfnl gtietksasv apftcktsea kkeempatkg
1081 gfsfgnvepa slpsasvfvl grteekqqep vtstslvfgk kadneepkcq pvfsfgnseq
1141 tkdensskst fsfsmtkpse keseqpakat fafgaqtstt adqgaakpvf sflnnssssss
1201 stpatsaggg ifgsstsssn ppvatfvfgq ssnpvsssaf gntaesstsq sllfsqdskl
1261 attsstgtav tpfvfgpgas snntttsgfg fqatttsssa gssfvfgtgp sapsaspafg
1321 anqtptfgqs qgasqpnppg fgsissstal fptgsqpapp tfgtvssssq ppvfgqpsq
1381 safgsgttpn sssafqfgss ttnfnftnns psgvfttfgan sstpaasaqp sgsggfpfnq
1441 spaaftvgsn gknvfsssgt sfsgrkikta vrrrk
```

Nup62 (human) Locus and Accession No. P37198

(SEQ ID NO: 2)

```
   1 msgfnfggtg aptggftfgt aktatttpat gfsfstsgtg gfnfgapfqp atstpstglf
  61 slatqtpatq ttgftfgtat lasggtgfsl gigasklnls ntaatpaman psgfglqssn
 121 ltnaisstvt ssqgtaptgf vfgpsttsva pattsggfsf tggstaqpsg fnigsagnsa
 181 qptapatlpf tpatpaatta gatqpaaptp tatitstgps ifasiatapt ssattglslc
 241 tpvttagapt agtqgfslka pgaasgtstt tstaatatat ttssssttgf alnlkplapa
 301 gipsntaaav tappgpgaaa gaaassamty aqleslinkw sleledqerh flqqatqvna
 361 wdrtlienge kitslhreve kvkidqkrld qeldfilsqq keledllspl eelvkeqsgt
 421 iylqhadeer ektyklaeni daqlkrmaqd lkdiiehlnt sgapadtsdp lqqickilna
 481 hmdsiqwidq nsallqrkve evtkvcegrr keqersfrit fd
```

Tpr (human) Locus and Accession No. P 12270

(SEQ ID NO: 3)

```
   1 maavlqqvle rtelnklpks vqnklekfla dqqseidglk grhekfkves eqqyfeiekr
  61 lshsqerlvn etrecqslrl eleklnnqlk alteknkele iaqdrniaiq sqftrtkeel
 121 eaekrdlirt nerlsqeley ltedvkrlne klkesnttkg elqlkldelq asdvsvkyre
 181 krleqekell hsqntwlnte lktktdella lgrekqneil elkcnlenkk eevsrleeqm
 241 nqlktsnehl qkhvedlltk lkeakeqqas meekfhneln ahiklsnlyk saaddseaks
 301 neltraveel hkllkeaqea nkaiqdhlle veqskdqmek emlekigrle kelenandll
 361 satkrkgail seeelaamsp taaavakivk pgmkltelyn ayvetqdqll leklenkrin
 421 kyldeivkev eakapilkrq reeyeraqka vaslsvkleq amkeiqrlqe dtdkankqss
 481 vlerdnrrme iqvkdlsqqi rvllmeleea rgnhvirdee vssadissss evisqhlvsy
 541 rnieelqqqn qrllvalrel getrereeqe ttsskitelq lklesaltel eqlrksrqhq
 601 mqlvdsivrq rdmyrillsq ttgvaiplha ssldvslas tpkrpstsqt vstpapvpvi
 661 esteaieaka alkqlqeife nykkekaene kiqneqlekl qeqvtdlrsq ntkistqldf
 721 askryemlqd nvegyrreit slherngklt attqkqeqii ntmtqdlrga neklavaevr
 781 aenlkkekem lklsevrlsq qresllaeqr gqnllltnlq tiqgilerse tetkqrlssq
 841 iekieheish lkkkleneve qrhtltrnld vqlldtkrql dtetnlhlnt kelllknaqke
```

-continued

```
 901 iatlkqhlsn mevqvasqss qrtgkgqpsn kedvddlvsq lrqteeqvnd lkerlktsts
 961 nveqyqamvt sleeslnkek qvteevrkni evrlkesaef qtqlekklme vekekqelqd
1021 dkrraiesme qqlselkktl ssvqnevqea lqrastalsn eqqarrdcqe qakiaveaqn
1081 kyerelmlha advealqaak eqvskmasvr qhleettqka esqlleckas weerermlkd
1141 evskcvcrce dlekqnrllh dqieklsdkv vasvkegvqg plnvslseeg ksqeqileil
1201 rfirrekeia etrfevaqve slryrqrvel lerelqeled slnaerekvq vtaktmaqhe
1261 elmkktetmn vvmetnkmlr eekerleqdl qqmqakvrkl eldilplqea naelseksgm
1321 lqaekkllee dvkrwkarnq hlvsqqkdpd teeyrkllse kevhtkriqq lteeigrlka
1381 eiarsnaslt nnqnliqslk edlnkvrtek etiqkdldak iidiqekvkt itqvkkigrr
1441 yktqyeelka qqdkvmetsa qssgdhqeqh vsvqemqelk etlnqaetks kslesqvenl
1501 qktlsekete arnlqeqtvq lqselsrlrq dlqdrttqee qlrqqiteke ektrkaivaa
1561 kskiahlagv kdqltkenee lkqrngaldq qkdeldvrit alksqyegri srlerelreh
1621 qerhleqrde pqepsnkvpe qqrqitlktt pasgergias tsdppptanik ptpvvstpsk
1681 vtaaamaqnk stprasirpm vtpatvtnpt ttptatvmpt tqvesqeamq segpvehvpv
1741 fgstsgsvrs tspnvqpsis qpiltvqqqt qatafvqptq qshpqiepan qelssnivev
1801 vqsspverps tstavfgtvs atpssslpkr treeeedsti easdqvsddt vemplpkklk
1861 svtpvgteee vmaeestdge vetqvynqds qdsigegvtq gdytpmedse etsqslqidl
1921 gplqsdqqtt tssqdgqgkg ddvividsdd eeedeedddd dedtgmgde gedsnegtgs
1981 adgndgyead daeggdgtdp gteteesmgg gegnhraads qnsgegntga aessfsqevs
2041 reqqpssase rqaprapqsp rrpphplppr ltihappqel gppvqriqmt rrqsvgrglq
2101 ltpgiggmqq hffddedrtv pstptlvvph rtdgfaeaih spqvagvprf rfgppedmpq
2161 tssshsdlgq lasqgglgmy etplflahee esggrsvptt plqvaapvtv ftesttsdas
2221 ehasqsvpmv ttstgtlstt netatgddgd evfveaeseg isseagleid sqqeeepvqa
2281 sdesdlpsts qdppssssvd tsssqpkpfr rvrlqttlrq qvrqrqfnrq rgvshamggr
2341 gginrgnin
```

Lamin A/C (human) Locus and Accession No. P02545

(SEQ ID NO: 4)

```
  1 metpsqrrat rsgaqasstp lsptritrlq ekedlqelnd rlavyidrvr sletenaglr
 61 lriteseevv srevsgikaa yeaelgdark tldsvakera rlqlelskvr eefkelkarn
121 tkkegdliaa qarlkdleal lnskeaalst alsekrtleg elhdlrgqva kleaalgeak
181 kqlqdemlrr vdaenrlqtm keeldfqkni yseelretkr rhetriveid ngkqrefesr
241 ladalqelra qhedqveqyk kelektysak ldnarqsaer nsnlvgaahe elqqsririd
301 slsaqlsqlq kqlaakeakl rdledslare rdtsrrllae keremaemra rmqqqldeyq
361 elldiklald meihayrkll egeeerlrls psptsqrsrg rasshssqtq gggsvtkkrk
421 lestesrssf sqhartsgrv aveevdeegk fvrlrnksne dqsmgnwqik rqngddpllt
481 yrfppkftlk agqvvtiwaa gagathsppt dlvwkaqntw gcgnslrtal instgeevam
541 rklvrsvtvv eddededgdd llhhhgshc sssgdpaeyn lrsrtvlcgt cgqpadkasa
601 sgsgaqvggp issgssassv tvtrsyrsvg gsgggsfgdn lvtrsyllgn ssprtqspqn
661 csim
```

Lamin B2 (human) Locus and Accession No. NP_116126

(SEQ ID NO: 5)

```
  1 matplpgrag gpatplsptr lsrlqekeel relndrlahy idrvralele ndrllllkise
```

-continued

```
 61 keevttrevs gikalyesel adarrvldet arerariqie igklraelde vnksakkreg
121 eltvaqgrvk dleslfhrse velaaalsdk rqlesdvael raqlakaedg havakkqlek
181 etlmrvdlen rcqslqeeld frksvfeeev retrrrherr lvevdssrqq eydfkmaqal
241 eelrsqhdeq vrlykleleq tyqakldsak lssdqndkaa saareelkea rmrleslsyq
301 lsqlqkqasa aedrirelee amagerdkfr kmldakeqem temrdvmqqq laeyqelldv
361 klaldmeina yrkllegeee rlklspspss rvtvsratss ssgslsatgr lgrskrkrle
421 veeplgsgps vlgtgtggsg gfhlaqqasa sgsvsieeid legkfvqlkn nsdkdqslgn
481 wrikrqvleg eeiaykftpk yilragqmvt vwaagagvah sppstlvwkg qsswgtgesf
541 rtvlvnadge evamrtvkks svmrenenge eeeeeaefge edlfhqqgdp rttsrqcyvm
```

Emerin (human) Locus and Accession No. P50402

(SEQ ID NO: 6)
```
  1 mdnyadlsdt elttllrryn iphgpvvgst rrlyekkife yetqrrrlsp psssaassys
 61 fsdlnstrgd admydlpkke dallyqskgy nddyyeesyf ttrtygepes agpsravrqs
121 vtsfpdadaf hhqvhdddll ssseeeckdr erpmygrdsa yqsithyrpv sasrssldls
181 yyptssstsf mssssssssw ltrrairpen rapgaglgqd rqvplwgqll lflvfvivlf
241 fiyhfmqaee gnpf
```

Calnexin (human) Locus and Accession No. AAA36125

(SEQ ID NO: 7)
```
  1 megkwllcml lvlgtaivea hdghdddvid ieddlddvie evedskpdtt appsspkvty
 61 kapvptgevy fadsfdrgtl sgwilskakk ddtddeiaky dgkweveemk esklpgdkgl
121 vlmsrakhha isaklnkpfl fdtkplivqy evnfqngiec ggayvkllsk tpelnldqfh
181 dktpytimfg pdkcgedykl hfifrhknpk tgiyeekhak rpdadlktyf tdkkthlytl
241 ilnpdnsfei lvdqsvvnsg nllndmtppv npsreiedpe drkpedwder pkipdpeavk
301 pddwdedapa kipdeeatkp egwlddepey vpdpdaekpe dwdedmdgew eapqianprc
361 esapgcgvwq rpvidnpnyk gkwkppmidn psyqgiwkpr kipnpdffed lepfrmtpfs
421 aiglelwsmt sdiffdnfii cadrrivddw andgwglkka adgaaepgvv gqmieaaeer
481 pwlwvvyilt valpvflvil fccsgkkqts gmeykktdap qpdvkeeeee keeekdkgde
541 eeegeeklee kqksdaeedg gtvsqeeedr kpkaeedeil nrsprnrkpr re
```

BiP (human) Locus and Accession No. P11021

(SEQ ID NO: 8)
```
  1 mklslvaaml lllsaaraee edkkedvqtv vgidlgttys cvgvfkngrv eiiandqgnr
 61 itpsyvaftp egerligdaa knqltsnpen tvfdakrlig rtwndpsvqq dikflpfkvv
121 ekktkpyiqv digggqtktf apeeisamvl tkmketaeay lgkkvthavv tvpayfndaq
181 rqatkdagti aglnvmriin eptaaaiayg ldkregekni lvfdlgggtf dvslltidng
241 vfevvatngd thlggedfdq rvmehfikly kkktgkdvrk dnravqklrr evekakrals
301 sqhqarieie sfyegedfse tltrakfeel nmdlfrstmk pvqkvledsd lkksdideiv
361 lvggstripk iqqlvkeffn gkepsrginp deavaygaav qagvlsgdqd tgdlvlldvc
421 pltlgietvg gvmtkliprn ttvptkksqi fstasdnqpt vtikvyeger pltkdnhllg
481 tfdltgippa prgvpqievt feidvngilr vtaedkgtgn knkititndq nrltpeeier
541 mvndaekfae edkklkerid trnelesyay slknqigdke klggklssed ketmekavee
601 kiewleshqd adiedfkakk keleeivqpi isklygsagp pptgeedtae kdel
```

PDI (human) Locus and Accession No. P07237

(SEQ ID NO: 9)
```
  1 mlrrallcla vaalvradap eeedhvlvlr ksnfaealaa hkyllvefya pwcghckala
```

-continued

```
  61 peyakaagkl kaegseirla kvdateesdl aqqygvrgyp tikffrngdt aspkeytagr
 121 eaddivnwlk krtgpaattl pdgaaaeslv essevavigf fkdvesdsak qflqaaeaid
 181 dipfgitsns dvfskyqldk dgvvlfkkfd egrnnfegev tkenlldfik hnqlplvief
 241 teqtapkifg geikthillf lpksvsdydq klsnfktaae sfkgkilfif idsdhtdnqr
 301 ileffglkke ecpavrlitl eeemtkykpe seeltaerit efchrflegk ikphlmsqel
 361 pedwdkqpvk vlvgknfedv afdekknvfv efyapwcqhc kqlapiwdkl getykdheni
 421 viakmdstan eveavkvhsf ptlkffpasa drtvidynge rtldgfkkfl esggqdgagd
 481 dddledleea eepdmeeddd qkavkdel
```

CLIMP63 (human) Locus and Accession No. NP_006816

(SEQ ID NO: 10)
```
   1 mpsakqrgsk qghgaaspse kgahpsggad dvakkpppap qqppppaph pqqhpqqhpq
  61 nqahgkgghr gggggggkss ssssasaaaa aaaasssasc srrlgralnf lfylalvaaa
 121 afsgwcvhhv leevqqvrrs hqdfsrqree lgqglqgveq kvqslqatfg tfesilrssq
 181 hkqdltekav kqgesevsri sevlqklqne ilkdlsdgih vvkdarerdf tslentveer
 241 lteltksind niaiftevqk rsqkeindmk akvasleese gnkqdlkalk eavkeiqtsa
 301 ksrewdmeal rstlqtmesd iytevrelvs lkqeqqafke aadterlalq alteklIrse
 361 esvsrlpeei rrleeelrql ksdshgpked ggfrhseafe alqqksqgld srlqhvedgv
 421 lsmqvasarq teslesllsk sqeheqrlaa lqgrleglgs seadqdglas tvrslgetql
 481 vlygdveelk rsvgelpstv eslqkvqeqv htllsqdqaq aarlppqdfl drlssldnlk
 541 asvsqveadl kmlrtavdsl vaysvkietn ennlesakgl lddlrndldr lfvkvekihe
 601 kv
```

Karyopherin beta 1 (human) Locus and Accession No. NP_002256

(SEQ ID NO: 11)
```
   1 melitilekt vspdrlelea aqkfleraav enlptflvel srvlanpgns qvarvaaglq
  61 iknsltskdp dikaqyqqrw laidanarre vknyvlqtlg tetyrpssas qcvagiacae
 121 ipvnqwpeli pqlvanvtnp nstehmkest leaigyicqd idpeqlqdks neiltaiiqg
 181 mrkeepsnnv klaatnalln sleftkanfd keserhfimq vvceatqcpd trvrvaalqn
 241 lvkimslyyq ymetymgpal faitieamks didevalqgi efwsnvcdee mdlaieasea
 301 aeqgrppeht skfyakgalq ylvpiltqtl tkqdendddd dwnpckaagv clmllatcce
 361 ddivphvlpf ikehiknpdw ryrdaavmaf gcilegpeps qlkplviqam ptlielmkdp
 421 svvvrdtaaw tvgricellp eeaaindvyla pllqcliegl saeprvasnv cwafsslaea
 481 ayeaadvadd qeepatycls ssfelivqkl lettdrpdgh qnnlrssaye slmeivknsa
 541 kdcypavqkt tlvimerlqq vlqmeshiqs tsdriqfndl qsllcatlqn vlrkvqhqda
 601 lqisdvvmas llrmfqstag sggvqedalm avstlvevlq geflkymeaf kpflgiglkn
 661 yaeyqvclaa vglvgdlcra lqsniipfcd evmqllleni gnenvhrsvk pqilsvfgdi
 721 alaiggefkk ylevvlntlq qasqaqvdks dydmvdylne lrescleayt givqglkgdq
 781 envhpdvmlv qprvefilsf idhiagdedh tdgvvacaag ligdlctafg kdvlklvear
 841 pmihellteg rrsktnkakt latwatkelr klknqa
```

GTP-binding nuclear protein Ran (human)
Locus and Accession No. P62826

(SEQ ID NO: 12)
```
   1 maaqgepqvq fklvlvgdgg tgkttfvkrh ltgefekkyv atlqvevhpl vfhtnrgpik
  61 fnvwdtagqe kfgglrdgyy iqaqcaiimf dvtsrvtykn vpnwhrdlvr vcenipivlc
```

```
-continued
121 qnkvdikdrk vkaksivfhr kknlqyydis aksnynfekp flwlarklig dpnlefvamp 181 alappevvmd palaaqyehd levaqttalp dedddl Gamma-tubulin (human) Locus and Accession No. AAF34188
                                                              (SEQ ID NO: 13)
  1 mpreiitlql gqcgnqiqfe fwkqlcaehg ispegiveef ategtdrkdv ffyqaddehy 61 ipravlldle prvihsilns pyaklynpen iylsehggga gnnwasgfsq gekihedifd 121 iidreadgsd slegfvichs iaggtgsglg syllerlndr ypkklvqtys vfpyqdemsd 181 vvvqpynsll tlkrltqnad cvvvldntal nriatdrlhi qnpsfsqinq lvstimsast 241 ttlrypgymn ndligliasl iptprlhflm tgytplttdq svasvrkttv ldvmrrllqp 301 knvmvstgrd rqtnhcyiai lniiqgevdp tqvhkslqri rerklanfip wgpasiqval 361 srkspylpsa hrvsglmman htsisslfes scqqfdklrk rdafleqfrk edmfkdnfde 421 mdrsrevvqe lideyhaatq pdyiswgtqe q
```

The methods of the present invention are carried out ex vivo.

This invention will be better understood from the Experimental Details, which follow. However, one skilled in the art will readily appreciate that the specific methods and results discussed are merely illustrative of the invention as described more fully in the claims that follow thereafter.

EXPERIMENTAL DETAILS

Materials and Methods

Human Endometrial Biopsies. Endometrial biopsies were obtained by informed consent from normally cycling women at two sites, Albert Einstein College of Medicine, Bronx, NY (site 1, 50 biopsies) and University of North Carolina School of Medicine, Chapel Hill, N.C. (site 2, 45 biopsies). The respective Institutional Review Boards approved the collection protocols. The site 1 protocol was described previously (Kittur et al., 2007). Endometrial tissue was fixed with 4% paraformaldehyde in phosphate buffered saline. Routine histological methods were used for paraffin embedding and sectioning of tissue at the Histotechnology and Comparative Pathology Facility of the Albert Einstein College of Medicine. 28 hematoxylin and eosin stained sections of site 1 biopsies were scored blinded for the cycle day by two independent histopathologists using classical criteria (Noyes et al., 1950). The site 2 protocol was identical, except all samples were obtained from normal volunteers and cycle timing was based on cycle day (proliferative) and urine LH surge identification (secretory). Cycle day was confirmed by a single investigator blinded to LH data using the same criteria of Noyes et al. (1950). No biopsies were reassigned to a different cycle day based on histological review.

Immunostaining of Tissue Sections. For immunostaining, sections on slides were first deparaffinized by heating at 60° C. for 20 min, and rehydrated as follows: twice in xylene (5min each), 100% ethanol (10 min), 95% ethanol (5 min), 80% ethanol (2 min), 70% ethanol (2 min), twice in distilled water (2 min each). For subsequent antigen retrieval, slides were microwave-heated at full power (2 min) in 10 mM sodium citrate (pH 6.0) and steamed in a rice cooker (20 min). After cooling to room temperature, slides were rinsed with phosphate buffered saline and processed for routine immunostaining as described except that the sections were not further permeabilized with detergent (Isaac et al., 1998). Nuclei were counterstained with DAPI (Sigma) 1 mg/ml.

Cryosectioning was performed by the method of Tokuyasu as described previously (Kittur et al., 2007). For light microscopy, 0.5 µm thick (semi-thin) cryosections were cut from the fixed tissue, picked up using 2.3 M sucrose and placed on glass coverslips. The sucrose was dissolved by incubating the sections in nanopure water. Sections were next permeabilized by the following treatment for 30 seconds each, xylene, 100% ethanol, 95% ethanol, 80% ethanol, 70% ethanol, and distilled water. The antigen retrieval and immunostaining was identical to that described above for the paraffin sections.

Tissue arrays used were 61 endometrial carcinomas (adenocarcinomas grade I-III) with normal controls (Cybrdi Inc., Frederick, Md.), multiple organs and normal tissue from 48 patients (Cybrdi Inc.), and 59 normal endometrial sections (Imgenex Corporation, San Diego, Calif.). Tissue cores on the array slides were formalin-fixed and processed for immunostaining as described above.

Antibodies. Mouse IgGs (Covance Research Products Inc., Princeton, N.J.) of mAb414 (Davis and Blobel, 1986) were used at 2 µg/ml for light and at 500 µg/ml for electron microscopy. The following primary antibodies were used on paraffin and cryosections at the dilutions indicated in parentheses: anti-calnexin rabbit polyclonal serum (SPA860 at 1:200; Assay Designs/StressGen, Ann Arbor, Mich.); anti-BiP mouse IgGs (10C3 anti-KDEL at 2.5 µg/ml, Assay Designs/StressGen); anti-PDI polyclonal serum (SPA860 at 1:200, Assay Designs/StressGen); anti-Sec61b rabbit serum (1:200 using RNAse)(Fons et al., 2003; Snapp et al., 2004); anti-human Nopp140 rabbit polyclonal serum (RS8 1:500)(Kittur et al., 2007); anti-human NAP57 rabbit polyclonal serum (RU8 at 1:200)(Darzacq et al., 2006); anti-fibrillarin mouse monoclonal IgG (clone D77 at 1 µg/ml)(Aris and Blobel, 1988); anti-nucleolin mouse ascites fluid (clone 7G2 at 1:1000)(Pinol-Roma, 1999); anti-UBF1 rabbit polyclonal serum (1:100, from Larry Rothblum, University of Oklahoma Medical College, Oklahoma City, Okla.); anti-SC35 mouse ascites fluid (1:1000, Sigma Aldrich Corp., St. Louis, Mo.); anti-coilin mouse ascites fluid (clone 5P10 at 1:1000) (Almeida et al., 1998); anti-RNA polymerase II C-terminal domain mouse monoclonal culture supernatants (clone H14, IgM undiluted, initiating) and (clone H5, IgG undiluted, elongating)(Bregman et al., 1995); anti-Nup153 mouse monoclonal ascites fluid (clone 322 at 1:100)(Sukegawa and Blobel, 1993) and culture supernatant (clone SA1 at 1:10) (Bodoor et al., 1999); anti-Nup358 rabbit polyclonal serum (1:500)(Wu et al., 1995); anti-Tpr rabbit polyclonal serum (Tpr C at 1:300)(Frosst et al., 2002); anti-Nup62 goat polyclonal (sc-1916 at 1:20, Santa Cruz Biotechnology, Inc., Santa Cruz, Calif.); anti-Nup214 rabbit polyclonal serum (1:50, from Joseph Glavy, Stevens Institute of Technology; anti-lamin A/C rabbit polyclonal IgG (sc-20681 at 2 µg/ml, Santa Cruz Biotechnology, Inc.); anti-lamin A goat polyclonal IgG (sc-6214 at 4 µg/ml, Santa Cruz Biotechnology, Inc.); anti-lamin B1 rabbit polyclonal serum (1:1000)(Moss et al., 1999); anti-lamin B2 mouse monoclonal IgG (clone LN43 at 100 µg/ml, Chemicon International Inc., Temecula, Calif.); anti-LAP2b mouse monoclonal IgG (5 µg/ml, BD Transduction Laboratories, San Diego, Calif.); anti-emerin mouse monoclonal culture supernatant (clone 4G5 at 1:20, Novocastra Laboratories Ltd., Newcastle upon Tyne, UK); anti-CLIMP63 rabbit polyclonal serum (1:200)(Schweizer et al., 1995); anti-p115 rabbit polyclonal serum (1:500) (Mukherjee et al., 2007); anti-GM130 mouse monoclonal IgG (clone 35 at 1.25 µg/ml, BD Transduction Laboratories); anti-progesterone receptor rabbit polyclonal IgG (sc-538 at 2 µg/ml, Santa Cruz Biotechnology Inc., and ab15509 at 2 µg/ml, Abcam Inc., Cambridge, Mass.); anti-estrogen receptor a rabbit polyclonal IgG (sc-542 at 2 µg/ml, Santa Cruz Biotechnology Inc.); fluorescently-labeled wheat germ agglutinin (WGA at 0.1 mg/ml, Sigma Aldrich Corp.). Although all antibodies stained cells in their predicted pattern, the lack of NCS staining in some cases could result from masking or loss of an epitope specifically in NCSs.

DNA was stained with 4',6-diaminidino-2-phenylindole dihydrochloride (DAPI at 1 µg/ml, Sigma Aldrich Corp.). Secondary antibodies for immunofluorescence against IgGs were Cy3 or Cy5 conjugated donkey anti-mouse, Cy2 conjugated donkey anti-rabbit, and Cy3 conjugated donkey anti-goat (1:200, Jackson ImmunoResearch Labs Inc., West Grove, Pa.); and AlexaFluor488 conjugated goat anti-mouse IgMs (1:200, Invitrogen Corp., Carlsbad, Calif.).

Imaging. All imaging was done at the Analytical Imaging Facility of the Albert Einstein College of Medicine. Epifluorescence of cryo- and paraffin sections was performed with the identical procedure and equipment as described recently (Kittur et al., 2007). Confocal laser scanning microscopy of paraffin sections was performed on a AOBS microscope (Leica, Mannheim, Germany) employing a 63×/1.4 NA planapo objective. Argon and helium-neon lasers provided lines at 488 nm and 543 nm for excitation of Cy2 and Cy3 fluorophores, respectively. Detection ranges were set to eliminate crosstalk between fluorophores. Image stacks were reconstructed in 3-dimenstions, enhanced, and analyzed using ImageJ software (National Institutes of Health, Bethesda Md.).

NCS Quantification. Quantitation of NCSs using mAb414 on paraffin sections was first established on a 3-dimensional training set of 11 endometrial specimens from luteal days 4-10. For this purpose the ~7 µm-thick sections were imaged with the confocal laser scanning microscope at 0.2 µm steps. In order to account for all NCSs, maximum projections of all stacks were reconstructed using the standard deviation method in ImageJ software (e.g., FIG. 1C'), and at least 600 epithelial cell nuclei for each biopsy were visually inspected for NCSs. The numbers from this analysis were related to those observed by two-dimensional analysis of the same biopsies using epifluorescence. In this manner, biopsies could easily be classified into three categories, those without NCSs (0%), those with low amounts (<10%), and those with plenty of NCSs, most commonly around 50% (~50%). All residual biopsies were analyzed using epifluorescence and assigned to one of these three categories. All scoring was done by at least two independent observers who were blinded as to the cycle day.

Results

Light Microscopic Detection of NCSs. In electron micrographs, NCSs are often associated with the nuclear envelope. Therefore, the presence in NCSs of proteins from the nuclear boundary was tested using indirect immunofluorescence on semi-thick frozen sections of human endometrium. Indeed, the monoclonal antibody 414 (mAb414), directed against a subset of nuclear pore complex proteins (Davis and Blobel, 1986), identified rings in the nuclei of some endometrial epithelial cells (FIG. 1A). The concentration of nucleoporins in these structures proved so high that the classical punctate NPC staining of the nuclear periphery only became evident upon overexposure of the image (FIG. 1A'). Although sometimes associated with nucleoli (FIG. 1A, arrowheads), these structures were distinct entities and had a darker ring shaped appearance in phase contrast images of these 0.5 µm-thick sections (FIG. 1A"). Nevertheless, like nucleoli, these rings did not stain for DNA (FIG. 1A'''). To determine their identity on an ultrastructural level, cryosections of human endometrium were stained with mAb414 followed by gold-labeled secondary antibodies. In addition to a NPC in an adjacent cell nucleus, mAb414 specifically and to a high density labeled NCSs but not adjacent nucleoli or other cellular compartments (FIG. 1B). Therefore, the rings identified at the light microscopic level were NCSs rendering mAb414 a specific marker for this nuclear organelle. The additional labeling of NPCs serves as a control for positive antibody staining and demarcation of cell nuclei.

To test the robustness of the mAb414 staining method and its applicability to more commonly available paraffin embedded tissue, paraffin sections of human endometrium were labeled. As in cryosections, mAb414 specifically stained NCSs and NPCs of epithelial cell nuclei whether visualized by epi-(FIG. 3B) or confocal fluorescence microscopy (FIG. 1C).

NCSs are Abundant Organelles Specific to Endometrial Epithelial Cells. In single 0.5 µm-thick cryosections or 0.2 µm-thick optical confocal planes of paraffin sections, NCSs are observed in only about 10% of epithelial cell nuclei (FIG. 1C), although clusters of NCS-positive nuclei can be observed (FIG. 1A). To assess the number of NCSs in entire nuclei, 7 µm-thick paraffin sections were stained with mAb414 and imaged across their entire thickness in 0.2 µm steps using confocal laser scanning microscopy. Whereas a NCS is visible in only one nucleus of a single optical plane (FIG. 1C), NCSs are detected in most nuclei of a maximum projection of all planes (FIG. 1C'). Analysis in this manner of 237 to 1034 epithelial cell nuclei per endometrial biopsy from 11 women (obtained between day 18 and 24 of an idealized 28 day cycle) revealed the following facts about NCSs. In total, 6701 nuclei contained 3065 NCSs corresponding to 46% of epithelial cell nuclei. In individual women, the number of NCSs varied between 27% and 58% with an average of 44% (+/−9). Most nuclei only contained a single NCS, although two and, in rare cases, up to five were also observed. All NCSs were apposed to the nuclear envelope and full-grown NCSs were uniform in size with a diameter of 1 µm. This overall abundance, and limitation in number per nucleus and size suggests a physiological role and a tight regulation of NCSs in the postovulatory endometrium.

NCSs were most abundant in epithelial glands but also present in luminal epithelium facing the uterine cavity. However, on no occasion were NCSs observed in nuclei of stromal cells. Moreover, analysis of tissue arrays containing six paraffin sections each of human esophagus, stomach, liver, colon, rectum, lung, kidney, and breast tissue, failed to reveal any NCSs when stained with mAb414. This is most remarkable for breast tissue, which, like endometrium, is under control of ovarian hormones. When endometrial tissue arrays from healthy and carcinoma patients were stained, 17% (n=59) of control specimens contained NCSs (which is in the expected range if biopsies were taken randomly throughout the cycle), whereas none of the carcinoma sections showed any. Therefore, NCSs are restricted to the nuclei of healthy endometrial epithelial cells.

Reportedly, NCSs are absent from animal endometria, even those of baboons (Clyman, 1963; MacLennan et al., 1971). To reevaluate these reports with the present robust NCS detection method, endometrial paraffin sections collected from 19 baboons during the height of receptivity were analyzed. Although the NPCs were readily detected by mAb414, no NCSs were identified. Hence, the NCS is a human-specific organelle.

Figures 2A, 2B, 2C, 2D, 2E, 2F, 2G, 2H:
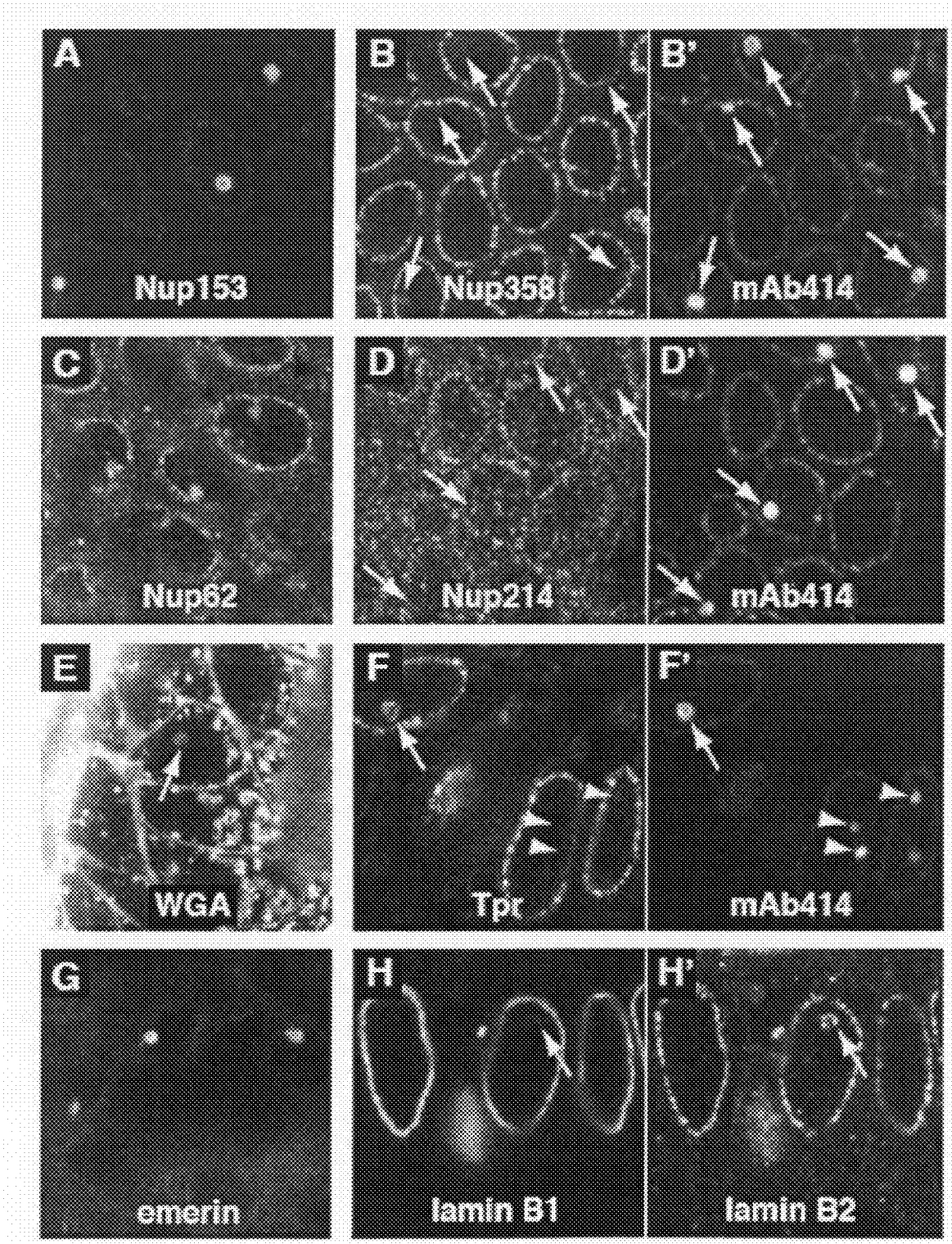
FIG. 2A-2N'. NCSs consist of a unique subset of NPC, and nuclear membrane and lamina proteins. Indirect immunofluorescence on semi-thin frozen sections of human luteal endometrium of antigens clearly present and/or enriched in NCSs (left column: A, C, E, G, I, K, M), of antigens absent from, barely detectable, or only in some NCSs (middle column: B, D, F, H, J, L, N), and of antigens clearly present in NCSs as double fluorescence control (right column: B', D', F', H', J', L', N'). The identity of all antigens is indicated on each panel. NCSs that are not obvious (E) or all in the double fluorescence series (two right columns) are indicated (arrows). In all cases the identity of NCSs was confirmed by double fluorescence and/or phase contrast microscopy. Note although mAb414 recognizes all four nucleoporins, only Nup153 (A) and Nup62 (C) but not Nup358 (B) nor Nup214 (D) are present in NCSs. Tpr is present in only some (F, arrow) but not other NCSs (arrowheads). Of the two inner nuclear membrane and lamina associated proteins emerin (G) and LAP2β (J), only emerin is enriched in NCSs. Nucleoli, identified by fibrillarin (N, arrowheads), are often adjacent to or surrounding NCSs (N', arrows) but do not overlap. Note the particularly high enrichment in NCSs of Nup153 (A), emerin (G), and lamin A/C (I), which at this exposure are barely detectable in their usual nuclear envelope locations. Magnification is identical in all panels; bar=5 μm (N').

The NCS is an Organelle of Unique Composition. In a candidate approach, colocalization with mAb414 was used for an initial compositional analysis of NCSs. First it was investigated if all nucleoporins recognized by mAb414 were present because no intact NPCs can be distinguished on an ultrastructural level. Indeed, when using nucleoporin-specific antibodies, only Nup153 and Nup62, but not Nup358 nor Nup214 were in NCSs (FIGS. 2A-D). Whereas the latter mark the cytosolic face of NPCs, the former constitute part of the central and nucleoplasmic face of NPCs (Tran and Wente, 2006). Therefore, the presence of Tpr was tested. Tpr is a nucleoporin interacting with Nup153 and forming the nuclear baskets of NPCs (Hase and Cordes, 2003; Krull et al., 2004). Interestingly, Tpr was enriched in some, mostly full-sized, NCSs but absent from others (FIG. 2F, compare arrows and arrowheads). This indicates the existence of two classes of NCSs that differ in composition and/or developmental stages, i.e., an early stage without and a mature one with Tpr, possibly mirroring the late NPC recruitment of Tpr in telophase (Hase and Cordes, 2003). Many nucleoporins, including Nup153 and Nup62, are post-translationally modified by single O-linked N-acetylglucosamine moieties, which bind the lectin wheat germ agglutinin (Davis and Blobel, 1986; Davis and Blobel, 1987). This lectin indeed recognized NCSs, presumably binding the sugar moieties of Nup153 and Nup62, which consequently must have been modified like their counterparts in NPCs (FIG. 2E). NPCs are anchored in the intermediate filament meshwork of the nuclear lamina that spans the inner nuclear envelope. Although lamins A/C were highly enriched in NCSs (FIGS. 2I and J'), lamin B1 was barely detectable (H), whereas B2 was present (H'). Of two integral membrane proteins specific to the inner nuclear membrane, emerin was most highly enriched in NCSs (FIG. 2G), whereas LAP2b was barely, if at all, detectable (J). This was surprising because both proteins belong to the lamin-interacting LEM-domain proteins (Lin et al., 2000; Wagner and Krohne, 2007). Unprecedented therefore, NCSs are composed of a specific subset of nuclear envelope proteins, part NPC, part lamina, and part inner membrane.

Figures 2I, 2J, 2K, 2L, 2M, 2N:
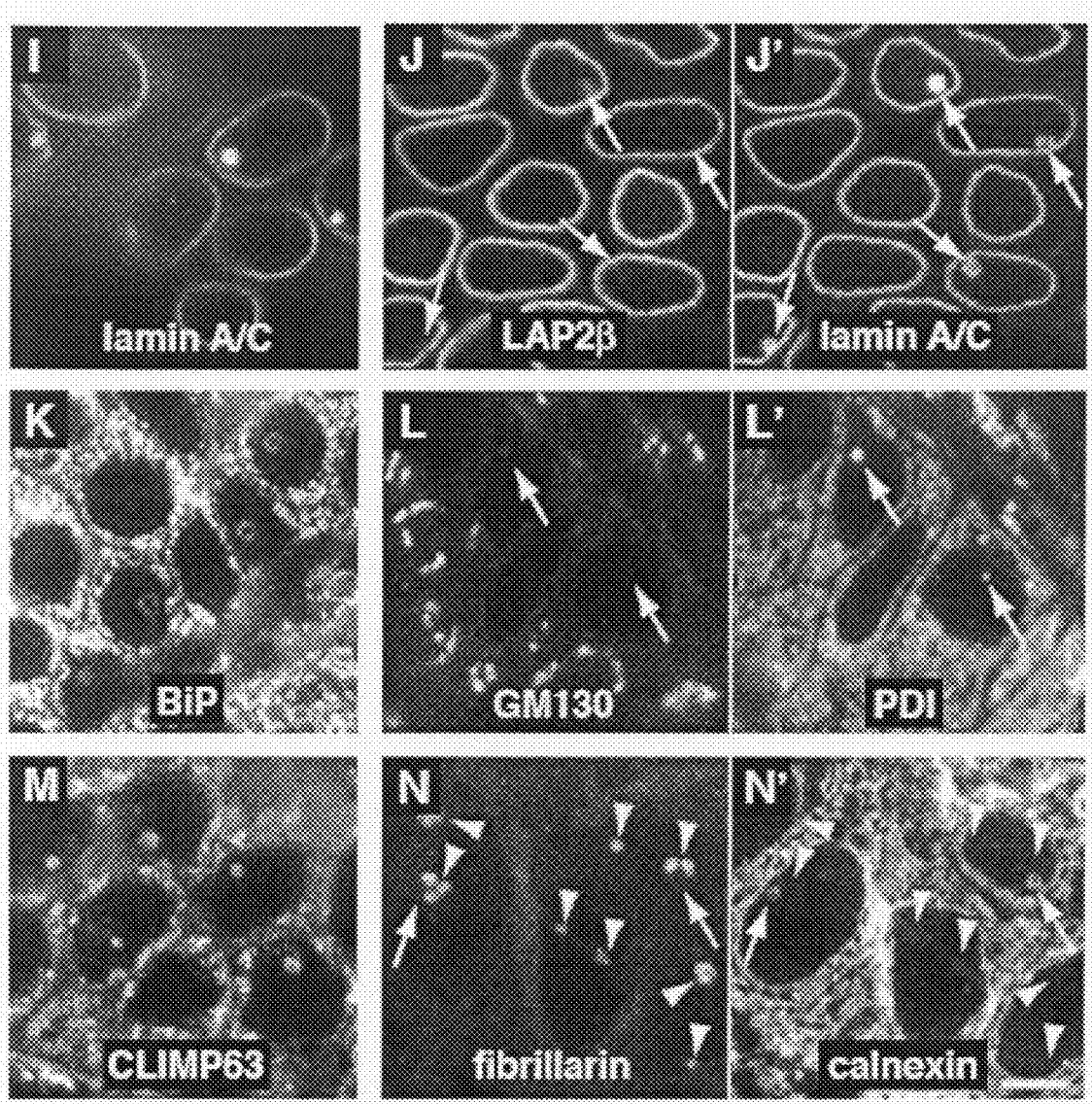

Apparently, the membrane tubules of the NCS are derived from the inner nuclear membrane, which is contiguous with that of the endoplasmic reticulum via the pore and the outer nuclear membrane. Therefore, the presence of endoplasmic reticulum proteins was tested for in NCSs. Both luminal, e.g., BiP and PDI, and integral membrane proteins, e.g., calnexin, could be detected in NCSs (FIG. 2K, L', and N'). Surprisingly, even the cytoskeleton linking integral membrane protein CLIMP63, which is concentrated in the endoplasmic reticulum but absent from the nuclear envelope (Klopfenstein et al., 2001), was prominent in NCSs (FIG. 2M). However, the rough endoplasmic reticulum marker protein Sec61, which is part of the protein-conducting channel, was not detected (Table 1). Similarly, antigens further along the secretory pathway, e.g., from the Golgi apparatus were absent from NCSs, specifically, GM130 and p115 (FIG. 2M and Table 1). Therefore, the NCS membrane system appears to derive from the nuclear envelope and the smooth endoplasmic reticulum.

As reflected in their name, NCSs are often surrounded by nucleoli in electron micrographs. A thorough analysis using three-dimensional confocal colocalization of mAb414 with the nucleolar marker Nopp140, which is not enriched in NCSs (Kittur et al., 2007), revealed 44% of NCSs (n=295) associated with nucleoli. Although only analyzed in 0.5 μm-thick frozen sections, there appeared to be an inverse relationship between the presence of Tpr in NCSs and their nucleolar association. To test if a common composition, as in the case of other nuclear membrane structures (Isaac et al., 2001; Kittur et al., 2007), was responsible for this association, additional nucleolar proteins were investigated for their presence in NCSs. Surprisingly, nucleolar proteins never concentrated in NCSs but often were apposed to them in nucleoli (FIG. 2N and Table 1). Therefore, the molecular basis of the NCS-nucleolus relationship remains to be elucidated. Finally, none of the markers for other nucleoplasmic domains or functions accumulated in NCSs, specifically, the Cajal body marker coilin, the nuclear speckle-specific splicing factor SC35, initiating or elongating RNA polymerase II, and the progesterone and estrogen receptor transcription factors (Table 1). Consequently, the NCS represents a nuclear organelle of distinct composition.

Figure 3A:
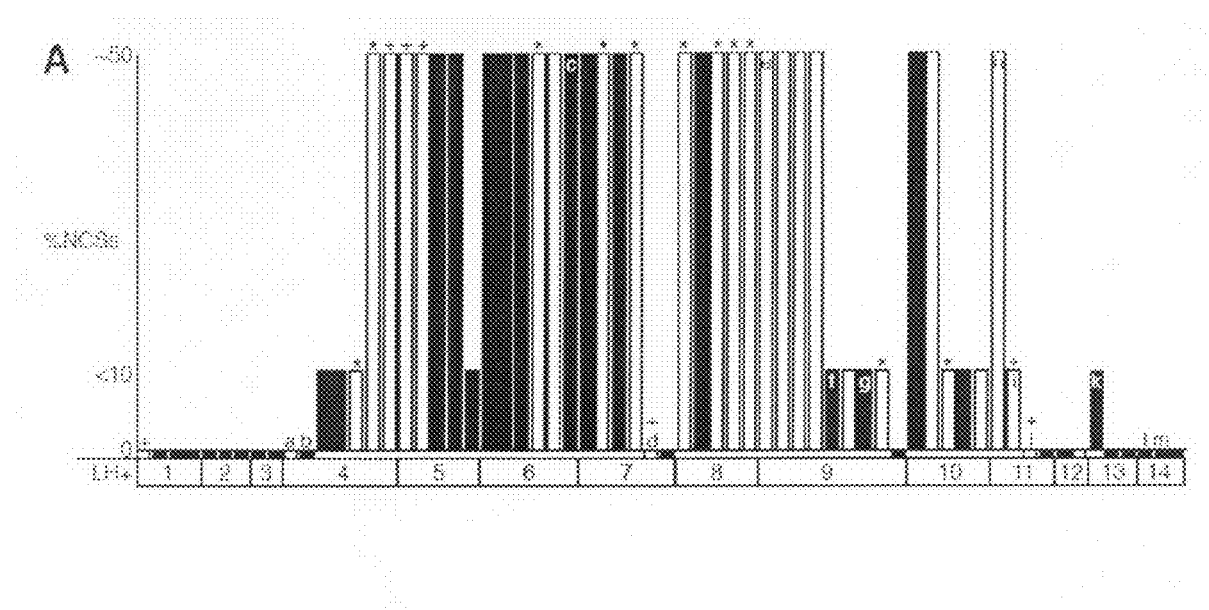
FIG. 3A-3C. The NCS marks the implantation window. (A) Histogram of 64 human endometrial biopsies collected on the indicated luteal days (LH+) and scored for the percentage of epithelial cell nuclei containing NCSs using three categories, none (0%), less than 10% (<10%), and between 10% and 60% but mostly around 50% (~50%). Where available, the luteal day was determined in the following order of priority, according to LH surge, classical histological criteria (+) (Noyes et al., 1950), and chronological day (*). Biopsies were considered out-of-phase if two methods differed by more than two days: (a) LH+4, chronological day (cd)=10, histological day (hd)=17, fibroid uterus; (b) LH+4, cd=15; (c) LH+6, cd=23; (d) menopause transition treated with hyper estrogen and hypo progesterone; (e) LH+9, hd=19, cd=26, 30-34d cycle; (f) LH+9, cd=27; (g) LH+9, cd=20; (h) LH+1 11, 34-37d cycle; (i) hd=25, cd=22, dysmenorrhea; (j) hd=25, cd=21; (k) LH+13, cd=30; (l) LH+14, cd=24; (m) LH+14, cd=25. (B) Representative mAb414 fluorescence micrographs for each category in (A) including a proliferative biopsy. Bar=20 μm. (C) Summary of the data in (A) expressed as percentage of biopsies on each luteal day containing NCSs (black squares, left y-axis) and the number of biopsies analyzed on each day (gray circles, right y-axis). Note only on luteal days 4-10 did over 70% of biopsies contain NCSs.
Figure 3B:
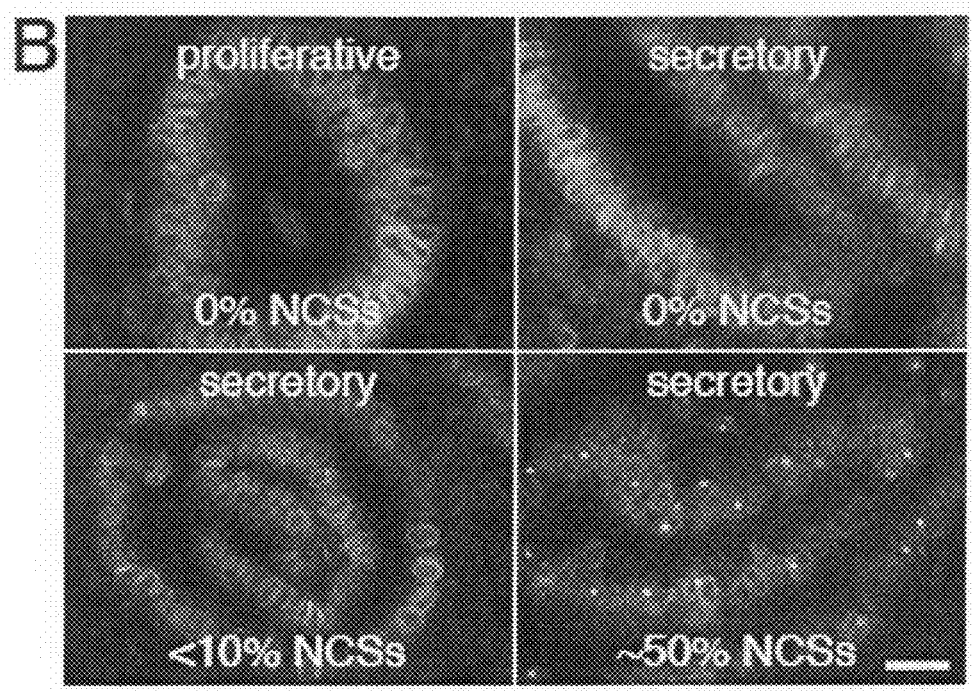
Figure 3C:
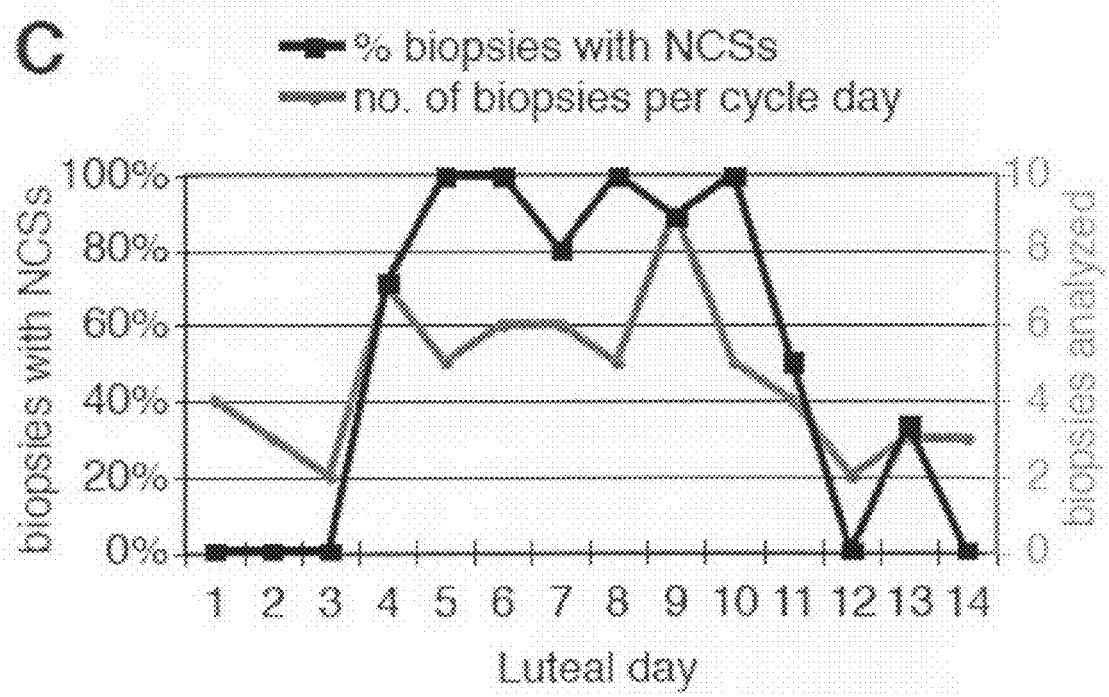

The NCS Marks the Implantation Window. Although previous electron microscopic studies agree that the NCS marks the postovulatory endometrium, the exact window of NCS appearance varies. Therefore, the present robust NCS detection method was tested on 95 endometrial biopsies from fertile women, 31 from the follicular and 64 from the luteal phase. NCSs were restricted to luteal days LH+4 to LH+13 and none were detected in any of the follicular phase biopsies (FIG. 3A and B). Whereas no NCSs were observed before day LH+4, after day LH+9, they appeared to gradually decline as the number with few and no NCSs increased. Although, across all days, one site had a slightly lower proportion of samples without NCSs, biopsies collected at two separate sites defined the same NCS window (FIG. 3A, black and white bars). Several biopsies were considered out-of-phase due to a more than two-day difference between dating methods, LH surge, histological dating, and chronological dating, or patients had irregular and/or long cycles (FIG. 3A, lettered biopsies). If all those biopsies were disregarded, NCSs were only observed on days LH+4 to LH+10, but none in the three days prior or four days after. In fact, even when considering all biopsies, over 70% of biopsies/day in that window contained NCSs, whereas thereafter their number dropped to 50% and below (FIG. 3C). In summary, the NCS appearance peaks on cycle days LH+5 to LH+9 (+/−1 day), i.e., days 19-23 (+/−1) of an idealized 28-day cycle define the NCS window.

TABLE 1

List of antigens tested for presence in NCSs.

| Compartment | Antigen | NCS |
|---|---|---|
| NPC | Nup153 | +++ |
|  | Nup62 | + |
|  | Nup358 | – |
|  | Nup214 | – |
|  | Tpr | +/– |
|  | WGA | + |
| Nuclear Envelope | Lamin A/C | +++ |
|  | Lamin A | + |
|  | Lamin B1 | (+) |
|  | Lamin B2 | + |
|  | Emerin | +++ |
|  | LAP2β | (+) |
| Endoplasmic Reticulum | Calnexin | + |
|  | BiP | + |
|  | PDI | + |
|  | CLIMP63 | + |
|  | Sec61 | – |
| Nucleolus | Nopp140 | – |
|  | NAP57 | – |
|  | Fibrillarin | – |
|  | Nucleolin | – |
|  | UBF1 | – |
| Nucleoplasm | Coilin | – |
|  | Pol II CTD S2-P[a] | – |
|  | Pol II CTD S5-P[b] | – |
|  | SC35 | – |
|  | Progesterone receptor | – |
|  | Estrogen receptor | – |
| Golgi | p115 | – |
|  | GM130 | – |

+++, highly enriched; +, present; –, absent; +/–, only in some; (+), barely detectable.
[a] Antibodies specific for the phosphorylated serine 2 of the carboxyl terminal domain of RNA polymerase II, which is characteristic for the initiating enzyme.
[b] Antibodies specific for the phosphorylated serine 5 of the carboxyl terminal domain of RNA polymerase II, which is characteristic for the elongating enzyme.

Discussion

The major impact of the present results is two-fold, the NCS detection assay provides a simple method for endometrial dating and the unique molecular composition of the NCS provides a basis for understanding complex interactions governing nuclear architecture.

Nuclear Organelles of Novel Composition. What is the NCS? The monoclonal antibody 414 is an excellent marker for NCSs. However, only a subset of the nucleoporins recognized by this antibody resides in NCSs, Nup153 and Nup62. Similarly, only some inner nuclear membrane (emerin) and lamina proteins (lamin A/C) are enriched in NCSs, whereas all tested proteins of the smooth endoplasmic reticulum are present. This selective composition of the NCS, together with its membrane tubules in the normally membrane-free nucleus, renders the NCS unique among nuclear organelles. Despite the analysis of only a sampling of envelope proteins, it is clear that NCSs are not a mere extension but a specialization of the nuclear envelope.

Although membranous structures have been previously observed in nuclei, they were all artificially induced and differ in composition from the physiological NCSs as detailed below. R-rings, which are induced by exogenous expression of the nucleolar protein Nopp140, are virtually indistinguishable from NCSs on an ultrastructural level hinting at a common derivation from the inner nuclear membrane (Isaac et al., 2001; Kittur et al., 2007). However, R-rings differ from NCSs in their composition, e.g., in their accumulation of nucleolar proteins that are absent from NCSs (Isaac et al., 2001; Kittur et al., 2007). Interestingly, overexpression of mammalian Nup153 and B-type lamins, which are both present in NCSs, and of the yeast Nup53p leads to intranuclear membrane formation (Bastos et al., 1996; Marelli et al., 2001; Prufert et al., 2004; Ralle et al., 2004). However, none of these proteins is overexpressed in NCS-positive cells because, unlike during their exogenous expression, nuclear envelope staining of these proteins is not increased compared to that of neighboring, NCS-free cells. Additionally, where available, these membranes differ in composition, as the Nup153 induced structures lack Nup62 and lamins (data not shown), and Nup53p structures stain negative for mAb414 (Marelli et al., 2001). Moreover, membrane proliferation-appeared to be dependent on the permanent farnesylation of B-type lamins (Prufert et al., 2004; Ralle et al., 2004), but this modification is removed from the more highly NCS enriched A-type lamins. Finally, the presence of lamins and only some nucleoporins sets NCSs apart from annulate lamellae, intact NPCs embedded in register in lamin-free stacks of smooth endoplasmic reticulum (Chen and Merisko, 1988). Consequently, NCSs are distinct from all these nuclear structures.

What causes the formation of NCSs? Apparently, NCSs are induced by the action of progesterone, but steroid receptors are not enriched in NCSs (Table 1) (Kohorn et al., 1970; Kohorn et al., 1972; Pryse-Davies et al., 1979; Roberts et al., 1975). NCSs are only one of several precisely timed ultrastructural changes occurring in postovulation endometrial epithelial cells (Spornitz, 1992). The uniform size of NCSs of 1 μm and limited number of one per nucleus indicate that their growth is controlled and not a random proliferation. Unlike in artificial cases mentioned herein, NCSs are not induced by simple overexpression of one of its components. This is supported by gene expression profiling studies of human endometrium reporting no upregulation of any of the NCS components identified here or of nuclear structures altogether (Borthwick et al., 2003; Carson et al., 2002; Horcajadas et al., 2004; Kao et al., 2002; Mirkin et al., 2005; Riesewijk et al., 2003; Talbi et al., 2006). This is surprising considering that, based on extrapolations of fluorescence intensity measurements to the surfaces of entire NCSs and nuclear envelopes, the amount in the NCS of its most prominent constituents (Nup153, emerin, and lamin A/C) equals that of the entire nuclear envelope. Therefore, even the levels of those proteins need only increase two-fold to account for their bright fluorescence in NCSs. In a tissue-wide analysis this factor would be reduced by at least half due to the presence of NCS-free epithelial cells alone. Consequently, these proteins would escape the sensitivity of a gene profiling approach arguing for more sensitive, single cell based assays as reported here.

Markers for Uterine Receptivity. The identification of the first molecular markers for NCSs allowed development of a light microscopic assay for their detection. Application of this assay reveals a peak presence of NCSs in over 50% of endometrial epithelial cells or a ten-fold higher prevalence than was appreciated based on previous electron microscopic studies (Novotny et al., 1999; Ryder et al., 1995). Therefore, the present results establish the NCS as a major physiological hallmark of the postovulatory endometrium. Based on the analysis of 95 endometrial biopsies, NCSs define a six-day window, days 19-24 (+/–1) of an idealized 28 day cycle, that precedes and overlaps with the implantation window. This NCS window can now easily be determined in fresh and archival endometrial biopsies using our robust immunodetection assay.

Definition of the receptive period, the implantation window, of human endometrium has been and is a major challenge. This becomes particularly evident in artificial reproductive technologies that depend on accurate timing to increase the low average implantation rate of ~25% (de los Santos et al., 2003). Long-standing histological makers of uterine receptivity are slowly giving way to molecular markers, although no single one has up to now been able to withstand the test of time (Aghajanova et al., 2007). Pinopodes, which are apical membrane protrusions thought to be critical for and present at the site of blastocyst attachment, persist through early menses and pregnancy (Acosta et al., 2000; Bentin-Ley et al., 1999; Nikas et al., 1995; Usadi et al., 2003). Additionally, the value of pinopodes as implantation markers has recently been questioned (Petersen et al., 2005; Quinn et al., 2007). With the development of the present assay, the NCS now combines a histological marker with molecular detection. The present application indicates that NCSs can be used as a hallmark of receptive endometrium as they define a luteal window that closely mirrors serum progesterone levels.

REFERENCES

Acosta, A. A., L. Elberger, M. Borghi, J. C. Calamera, H. Chemes, G. F. Doncel, H. Kliman, B. Lema, L. Lustig, and S. Papier. 2000. Endometrial dating and determination of the window of implantation in healthy fertile women. *Fertil. Steril.* 73:788-798.

Aghajanova L., A. E. Hamilton, L. C. Giudice. Uterine receptivity to human embryonic implantation: histology, biomarkers, and transcriptomics. *Semin. Cell Dev. Biol.* 2008 19:204-11. Epub 2007 Oct 22.

Almeida, F., R. Saffrich, W. Ansorge, and M. Carmo-Fonseca. 1998. Microinjection of anti-coilin antibodies affects the structure of coiled bodies. *J. Cell Biol.* 142:899-912.

Aris, J., and G. Blobel. 1988. Identification and characterization of a yeast nucleolar protein that is similar to a rat liver nucleolar protein. *J. Cell Biol.* 107:17-31.

Azadian-Boulanger, G., J. Secchi, F. Laraque, J. P. Raynaud, and E. Sakiz. 1976. Action of midcycle contraceptive (R 2323) on the human endometrium. *Am. J. Obstet. Gynecol.* 125:1049-1056.

Bastos, R., A. Lin, M. Enarson, and B. Burke. 1996. Targeting and function in mRNA export of nuclear pore complex protein Nup153. *J. Cell Biol.* 134:1141-1156.

Belgareh, N., G. Rabut, S. W. Bai, M. van Overbeek, J. Beaudouin, N. Daigle, O. V. Zatsepina, F. Pasteau, V. Labas, M. Fromont-Racine, J. Ellenberg, and V. Doye. 2001. An evolutionarily conserved NPC subcomplex, which redistributes in part to kinetochores in mammalian cells. *J. Cell Biol.* 154:1147-60.

Bentin-Ley, U., A. Sjogren, L. Nilsson, L. Hamberger, J. F. Larsen, and T. Horn. 1999. Presence of uterine pinopodes at the embryo-endometrial interface during human implantation in vitro. *Hum. Reprod.* 14:515-520.

Bodoor, K., S. Shaikh, D. Salina, W. H. Raharjo, R. Bastos, M. Lohka, and B. Burke. 1999. Sequential recruitment of NPC proteins to the nuclear periphery at the end of mitosis. *J. Cell Sci.* 112 (Pt 13):2253-64.

Borthwick, J. M., D. S. Charnock-Jones, B. D. Tom, M. L. Hull, R. Teirney, S. C. Phillips, and S. K. Smith. 2003. Determination of the transcript profile of human endometrium. *Mol. Hum. Reprod* 9:19-33.

Bregman, D. B., L. Du, S. van der Zee, and S. L. Warren. 1995. Transcription-dependent redistribution of the large subunit of RNA polymerase II to discrete nuclear domains. *J. Cell Biol.* 129:287-98.

Carson, D. D., E. Lagow, A. Thathiah, R. Al-Shami, M. C. Farach-Carson, M. Vernon, L. Yuan, M. A. Fritz, and B. Lessey. 2002. Changes in gene expression during the early to mid-luteal (receptive phase) transition in human endometrium detected by high-density microarray screening. *Mol. Hum. Reprod.* 8:871-9.

Chen, T. Y., and E. M. Merisko. 1988. Annulate lamellae: comparison of antigenic epitopes of annulate lamellae membranes with the nuclear envelope. *J Cell Biol.* 107: 1299-306.

Clyman, M. J. 1963. A new structure observed in the nucleolus of the human endometrial epithelial cell. *Am. J. Obstel. and Gynec.* 86:430-432.

Coutifaris, C., E. R. Myers, D. S. Guzick, M. P. Diamond, S. A. Carson, R. S. Legro, P. G. McGovern, W. D. Schlaff, B. R. Carr, M. P. Steinkampf, S. Silva, D. L. Vogel, and P. C. Leppert. 2004. Histological dating of timed endometrial biopsy tissue is not related to fertility status. *Fertil. Steril.* 82:1264-72.

Darzacq, X., N. Kittur, S. Roy, Y. Shav-Tal, R. H. Singer, and U. T. Meier. 2006. Stepwise RNP assembly at the site of H/ACA RNA transcription in human cells. *J. Cell Biol.* 173:207-18.

Davis, L. J., and G. Blobel. 1986. Identification and characterization of a nuclear pore complex protein. *Cell.* 45:699-709.

Davis, L. I., and G. Blobel. 1987. Nuclear pore complex contains a family of glycoproteins that includes p62: glycosylation through a previously unidentified cellular pathway. *Proc. Natl. Acad. Sci. U. S. A.* 84:7552-6.

de los Santos, M. J., A. Mercader, A. Galan, C. Albert, J. L. Romero, and A. Pellicer. 2003. Implantation rates after two, three, or five days of embryo culture. *Placenta.* 24 Suppl B:S13-9.

Dockery, P., K. Pritchard, M. A. Warren, T. C. Li, and I. D. Cooke. 1996. Changes in nuclear morphology in the human endometrial glandular epithelium in women with unexplained infertility. *Hum. Reprod.* 11:2251-2256.

Dubrauszky, V., and G. Pohlmann. 1960. Strukturveränderungen am Nukleolus von Korpusendoinetriuinzellen während der Sekretionsphase. *Naturwissenschaften.* 47:523-4.

Feria-Velasco, A., R. Aznar-Ramos, and A. Gonzalez-Angulo. 1972. Ultrastructural changes found in the endometrium of women using megestrol acetate for contraception. *Contraception.* 5:187-201.

Fons, R. D., B. A. Bogert, and R. S. Hegde. 2003. Substrate-specific function of the translocon-associated protein complex during translocation across the ER membrane. *J. Cell Biol.* 160:529-39.

Frosst, P., T. Guan, C. Subauste, K. Hahn, and L. Gerace. 2002. Tpr is localized within the nuclear basket of the pore complex and has a role in nuclear protein export. *J. Cell Biol.* 156:617-30.

Gore, B. Z., and M. Gordon. 1974. Fine structure of epithelial cell of secretory endometrium in unexplained primary infertility. *Fertil. Steril.* 25:103-107.

Hase, M. E., and V. C. Cordes. 2003. Direct interaction with nup153 mediates binding of Tpr to the periphery of the nuclear pore complex. *Mol. Biol. Cell.* 14:1923-40.

Horcajadas, J. A., A. Riesewijk, J. Martin, A. Cervero, S. Mosselman, A. Pellicer, and C. Simon. 2004. Global gene expression profiling of human endometrial receptivity. *J. Reprod. Immunol.* 63:41-9.

Isaac, C., J. W. Pollard, and U. T. Meier. 2001. Intranuclear endoplasmic reticulum induced by Nopp140 mimics the nucleolar channel system of human endometrium. *J. Cell Sci.* 114:4253-4264.

Isaac, C., Y. Yang, and U. T. Meier. 1998. Nopp140 functions as a molecular link between the nucleolus and the coiled bodies. *J. Cell Biol.* 142:319-329.

Kao, L. C., S. Tulac, S. Lobo, B. Imani, J. P. Yang, A. Germeyer, K. Osteen, R. N. Taylor, B. A. Lessey, and L. C. Giudice. 2002. Global gene profiling in human endometrium during the window of implantation. *Endocrinology.* 143:2119-2138.

Kittur, N., G. Zapantis, M. Aubuchon, N. Santoro, D. P. Bazett-Jones, and U. T. Meier. 2007. The Nucleolar Channel System of Human Endometrium Is Related to Endoplasmic Reticulum and R-Rings. *Mol. Biol. Cell.* 18:2296-2304.

Klopfenstein, D. R., J. Klumperman, A. Lustig, R. A. Kammerer, V. Oorschot, and H. P. Hauri. 2001. Subdomain-specific localization of CLIMP-63 (p63) in the endoplasmic reticulum is mediated by its luminal alpha-helical segment. *J. Cell Biol.* 153:1287-1300.

Kohorn, E. I., S. I. Rice, and M. Gordon. 1970. In vitro production of nucleolar channel system by progesterone in human endometrium. *Nature.* 228:671-672.

Kohorn, E. I., S. I. Rice, S. Hemperly, and M. Gordon. 1972. The relation of the structure of progestational steroids to nucleolar differentiation in human endometrium. *J. Clin. Endocrinol. Metab.* 34:257-264.

Krull, S., J. Thyberg, B. Bjorkroth, H. R. Rackwitz, and V. C. Cordes. 2004. Nucleoporins as components of the nuclear pore complex core structure and Tpr as the architectural element of the nuclear basket. *Mol. Biol. Cell.* 15:4261-77.

Lin, F., D. L. Blake, I. Callebaut, I. S. Skerjanc, L. Holmer, M. W. McBurney, M. Paulin-Levasseur, and H. J. Worman. 2000. MAN1, an inner nuclear membrane protein that shares the LEM domain with lamina-associated polypeptide 2 and emerin. *J. Biol. Chem.* 275:4840-7.

MacLennan, A. H., J. A. Harris, and R. M. Wynn. 1971. Menstrual cycle of the baboon. II. Endometrial ultrastructure. *Obstet. Gynecol.* 38:359-374.

Marelli, M., C. P. Lusk, H. Chan, J. D. Aitchison, and R. W. Wozniak. 2001. A Link between the Synthesis of Nucleoporins and the Biogenesis of the Nuclear Envelope. *J. Cell Biol.* 153:709-724.

Martel, D. 1981. Surface changes of the luminal uterine epithelium during the human mestrual cycle, a scanning microscopic study. In The endometrium: hormonal implants. J. Brux and J. P. Gantry, editors. Plenum, N.Y. 15-29.

Mirkin, S., M. Arslan, D. Churikov, A. Corica, J. I. Diaz, S. Williams, S. Bocca, and S. Oehninger. 2005. In search of candidate genes critically expressed in the human endometrium during the window of implantation. *Hum. Reprod.* 20:2104-17.

Moricard, R., and F. Moricard. 1964. Modifications cytoplasmiques et nucleaires ultrastructurales utérines au cours de l'état follico-lutéinique à glycogéne massif. *Gyn. Obst.* 63:203-219.

Moss, S. F., V. Krivosheyev, A. de Souza, K. Chin, H. P. Gaetz, N. Chaudhary, H. J. Worman, and P. R. Holt. 1999. Decreased and aberrant nuclear lamin expression in gastrointestinal tract neoplasms. *Gut.* 45:723-9.

Mukherjee, S., R. Chiu, S. M. Leung, and D. Shields. 2007. Fragmentation of the Golgi apparatus: an early apoptotic event independent of the cytoskeleton. *Traffic.* 8:369-78.

Murray, M. J., W. R. Meyer, R. J. Zaino, B. A. Lessey, D. B. Novotny, K. Ireland, D. Zeng, and M. A. Fritz. 2004. A critical analysis of the accuracy, reproducibility, and clinical utility of histologic endometrial dating in fertile women. *Fertil. Steril.* 81:1333-43.

Nikas, G., P. Drakakis, D. Loutradis, C. Mara-Skoufari, E. Koumantakis, S. Michalas, and A. Psychoyos. 1995. Uterine pinopodes as markers of the 'nidation window' in cycling women receiving exogenous oestradiol and progesterone. *Hum. Reprod.* 10: 1208-1213.

Norwitz, E. R., D. J. Schust, and S. J. Fisher. 2001. Implantation and the survival of early pregnancy. *N. Engl. J. Med.* 345:1400-1408.

Novotny, R., J. Malinsky, I. Oborna, and J. Dostal. 1999. Nuclear channel system (NCS) in normal endometrium and after hormonal stimulation. *Acta Univ. Palacki. Olomuc. Fac. Med.* 142:41-46.

Noyes, R. W., A. I. Hertig, and J. Rock. 1950. Dating the endometrial biopsy. *Fertil. Steril.* 1:3-25.

Petersen, A., U. Bentin-Ley, V. Ravn, K. Qvortrup, S. Sorensen, H. Islin, A. Sjogren, S. Mosselmann, and L. Hamberger. 2005. The antiprogesterone Org 31710 inhibits human blastocyst-endometrial interactions in vitro. *Fertil. Steril.* 83 Suppl 1:1255-63.

Pinol-Roma, S. 1999. Association of nonribosomal nucleolar proteins in ribonucleoprotein complexes during interphase and mitosis. *Mol. Biol. Cell.* 10:77-90.

Prufert, K., A. Vogel, and G. Krohne. 2004. The lamin CxxM motif promotes nuclear membrane growth. *J. Cell Sci.* 117:6105-16.

Pryse-Davies, J., T. A. Ryder, and M. L. MacKenzie. 1979. In vivo production of the nucleolar channel system in post menopausal endometrium. *Cell Tissue Res.* 203:493-498.

Quinn, C., E. Ryan, E. A. Claessens, E. Greenblatt, P. Hawrylyshyn, B. Cruickshank, T. Hannam, C. Dunk, and R. F. Casper. 2007. The presence of pinopodes in the human endometrium does not delineate the implantation window. *Fertil. Steril.* 87:1015-21.

Rabut, G., V. Doye, and J. Ellenberg. 2004. Mapping the dynamic organization of the nuclear pore complex inside single living cells. *Nat. Cell Biol.* 6:1114-21.

Ralle, T., C. Grund, W. W. Franke, and R. Stick. 2004. Intranuclear membrane structure formations by CaaX-containing nuclear proteins. *J. Cell Sci.* 117:6095-104.

Riesewijk, A., J. Martin, R. van Os, J. A. Horcajadas, J. Polman, A. Pellicer, S. Mosselman, and C. Simon. 2003. Gene expression profiling of human endometrial receptivity on days LH+2 versus LH+7 by microarray technology. *Mol. Hum. Reprod.* 9:253-64.

Roberts, D. K., D. V. Horbelt, and L. C. Powell, Jr. 1975. The ultrastructural response of human endometrium to medroxyprogesterone acetate. *Am. J. Obstet. Gynecol.* 123:811-818.

Ryder, T. A., M. A. Mobberley, and M. I. Whitehead. 1995. The endometrial nucleolar channel system as an indicator of progestin potency in HRT. *Maturitas.* 22:31-36.

Schweizer, A., J. Rohrer, J. W. Slot, H. J. Geuze, and S. Kornfeld. 1995. Reassessment of the subcellular localization of p63. *J. Cell Sci.* 108 (Pt 6):2477-85.

Snapp, E. L., G. A. Reinhart, B. A. Bogert, J. Lippincott-Schwartz, and R. S. Hegde. 2004. The organization of engaged and quiescent translocons in the endoplasmic reticulum of mammalian cells. *J. Cell Biol.* 164:997-1007.

Spornitz, U. M. 1992. The functional morphology of the human endometrium and decidua. *Adv. Anat. Embryol. Cell Biol.* 124:1-99.

Stewart, C. L., K. J. Roux, and B. Burke. 2007. Blurring the boundary: the nuclear envelope extends its reach. *Science.* 318:1408-12.

Sukegawa, J., and G. Blobel. 1993. A nuclear pore complex protein that contains zinc finger motifs, binds DNA, and faces the nucleoplasm. *Cell.* 72:29-38.

Talbi, S., A. E. Hamilton, K. C. Vo, S. Tulac, M. T. Overgaard, C. Dosiou, N. Le Shay, C. N. Nezhat, R. Kempson, B. A. Lessey, N. R. Nayak, and L. C. Giudice. 2006. Molecular phenotyping of human endometrium distinguishes menstrual cycle phases and underlying biological processes in normo-ovulatory women. *Endocrinology.* 147:1097-121.

Terry, L. J., E. B. Shows, and S. R. Wente. 2007. Crossing the nuclear envelope: hierarchical regulation of nucleocytoplasmic transport. *Science.* 318:1412-6.

Terzakis, J. A. 1965. The nucleolar channel system of the human endometrium. *J. Cell Biol.* 27:293-304.

Tran, E. J., and S. R. Wente. 2006. Dynamic nuclear pore complexes: life on the edge. *Cell.* 125:1041-53.

Trinkle-Mulcahy, L., and A. I. Lamond. 2007. Toward a high-resolution view of nuclear dynamics. *Science.* 318:1402-7.

Usadi, R. S., M. J. Murray, R. C. Bagnell, M. A. Fritz, A. I. Kowalik, W. R. Meyer, and B. A. Lessey. 2003. Temporal and morphologic characteristics of pinopod expression across the secretory phase of the endometrial cycle in normally cycling women with proven fertility. *Fertil. Steril.* 79:970-4.

Wagner, N., and G. Krohne. 2007. LEM-Domain proteins: new insights into lamin-interacting proteins. *Int. Rev. Cytol.* 261:1-46.

Wilcox, A. J., D. D. Baird, and C. R. Weinberg. 1999. Time of implantation of the conceptus and loss of pregnancy. *N. Engl. J. Med.* 340:1796-9.

Wu J, M J Matunis, D Kraemer, G Blobel. E Coutavas. 1995. Nup358, a cytoplasmically exposed nucleoporin with peptide repeats, Ran-GTP binding sites, zinc fingers, a cyclophilin A homologous domain, and a leucine-rich region. *J. Biol. Chem.* 270:14209-13.

Wynn, R. M. 1967. Intrauterine devices: effects on ultrastructure of human endometrium. *Science.* 156:1508-1510.

What is claimed is:

1. A method of assaying for the presence or absence of nucleolar channel systems (NCSs) in an endometrial tissue sample, where the method comprises contacting the tissue sample with an agent that is specific for a protein selected from the group consisting of Nup153, Nup62, Lamin A/C, Lamin A, Lamin B2, Emerin, Calnexin, Binding immunoglobulin Protein (BiP), Protein disulfide isomerase (PDI), and CLIMP63, wherein the agent is an antibody or an antibody fragment, and wherein the presence of the protein within nuclei of endometrial epithelial cells indicates the presence of NCSs in the endometrial tissue sample and wherein the absence of the protein within nuclei of endometrial epithelial cells indicates the absence of NCSs in the endometrial tissue sample.

2. The method of claim 1, wherein the agent binds to Nup153, Lamin A/C or Emerin.

3. The method of claim 1, wherein the presence of NCSs indicates that the endometrium is in a state that is receptive for implantation of an embryo.

4. The method of claim 1, wherein the tissue sample is obtained from the endometrium of a woman between day 18 and day 24 of a 28 day menstrual cycle, where day 1 of the cycle is defined as the first day of menstrual blood loss, and wherein the absence of NCSs indicates that the endometrium is not in a state that is receptive for implantation of an embryo.

5. The method of claim 1, wherein the tissue sample is obtained from the endometrium of a woman between day 19 and day 22 of a 28 day menstrual cycle, where day 1 of the cycle is defined as the first day of menstrual blood loss, and wherein the absence of NCSs indicates that the endometrium is not in a state that is receptive for implantation of an embryo.

6. The method of claim 1, wherein the tissue sample is obtained from the endometrium of a woman between day 4 and day 9 of the luteal phase of the menstrual cycle, and wherein the absence of NCSs indicates that the endometrium is not in a state that is receptive for implantation of an embryo.

7. The method of claim 1, wherein the tissue sample is obtained from the endometrium of a woman between day 5 and day 8 of the luteal phase of the menstrual cycle, and wherein the absence of NCSs indicates that the endometrium is not in a state that is receptive for implantation of an embryo.

8. The method of claim 1, wherein the presence or absence of the protein is determined using a light microscope.

9. A method of determining whether or not a postovulatory human endometrium is in a state that is receptive for implantation of a human embryo, the method comprising contacting a tissue sample from the endometrium with an agent that binds to nucleolar channel systems (NCSs), wherein the presence of NCSs indicates that the endometrium is in a state that is receptive for implantation of an embryo and the absence of NCSs indicates that the endometrium is not in a state that is receptive for implantation of an embryo, wherein the agent that binds to NCSs is an antibody or an antibody fragment and wherein the agent binds to Nup153, Nup62, Lamin A/C, Lamin A, Lamin B2, Emerin, Calnexin, Binding immunoglobulin Protein (BiP), Protein disulfide isomerase (PDI) or CLIMP63 within the nuclei of endometrial epithelial cells from the tissue sample.

10. The method of claim 9, wherein the tissue sample is obtained from the endometrium of a woman between day 18 and day 24 of a 28 day menstrual cycle, where day 1 of the cycle is defined as the first day of menstrual blood loss.

11. The method of claim 9, wherein the tissue sample is obtained from the endometrium of a woman between day 19 and day 22 of a 28 day menstrual cycle, where day 1 of the cycle is defined as the first day of menstrual blood loss.

12. The method of claim 9, wherein the agent binds to Nup153, Lamin A/C or Emerin.

13. The method of claim 9, wherein the presence of NCSs is detected between day 18 and day 24 of a 28 day menstrual cycle, where day 1 of the cycle is defined as the first day of menstrual blood loss.

14. The method of claim 9, wherein the presence of NCSs is detected between day 19 and day 22 of a 28 day menstrual cycle, where day 1 of the cycle is defined as the first day of menstrual blood loss.

15. The method of claim 9, wherein the presence of NCSs is detected between day 4 and day 9 of the luteal phase of the menstrual cycle.

16. The method of claim 9, wherein the presence of NCSs is detected between day 5 and day 8 of the luteal phase of the menstrual cycle.

* * * * *